(12) United States Patent
Fallen et al.

(10) Patent No.: US 11,923,078 B2
(45) Date of Patent: Mar. 5, 2024

(54) SEMI-AUTONOMOUS MEDICAL SYSTEMS AND METHODS

(71) Applicant: Terumo Cardiovascular Systems Corporation, Ann Arbor, MI (US)

(72) Inventors: David Fallen, Springdale, PA (US); Dean R. Marshall, Nashville, MI (US)

(73) Assignee: Terumo Cardiovascular Systems Corporation, Ann Arbor, MI (US)

( * ) Notice: Subject to any disclaimer, the term of this patent is extended or adjusted under 35 U.S.C. 154(b) by 609 days.

(21) Appl. No.: 17/085,745

(22) Filed: Oct. 30, 2020

(65) Prior Publication Data

US 2021/0134451 A1    May 6, 2021

Related U.S. Application Data

(60) Provisional application No. 62/929,134, filed on Nov. 1, 2019.

(51) Int. Cl.
| | | |
|---|---|---|
| *G16H 40/40* | (2018.01) | |
| *G16H 10/60* | (2018.01) | |
| *G16H 20/40* | (2018.01) | |
| *G16H 40/63* | (2018.01) | |
| *G16H 50/20* | (2018.01) | |
| *G16H 70/20* | (2018.01) | |

(52) U.S. Cl.
CPC ............ *G16H 40/40* (2018.01); *G16H 10/60* (2018.01); *G16H 20/40* (2018.01); *G16H 40/63* (2018.01); *G16H 50/20* (2018.01); *G16H 70/20* (2018.01)

(58) Field of Classification Search
None
See application file for complete search history.

(56) References Cited

U.S. PATENT DOCUMENTS

| | | |
|---|---|---|
| 5,817,007 A | 10/1998 | Fodgaard et al. |
| 6,423,022 B1 | 7/2002 | Roeher et al. |
| 6,691,047 B1 | 2/2004 | Fredericks |
| 6,692,518 B2 | 2/2004 | Carson |
| 6,775,577 B2 | 8/2004 | Crnkovich et al. |
| 7,038,588 B2 | 5/2006 | Boone et al. |
| 7,336,997 B2 | 2/2008 | Fukui |

(Continued)

FOREIGN PATENT DOCUMENTS

| | | |
|---|---|---|
| CN | 209916851 | 1/2020 |
| EP | 1900384 | 3/2008 |

(Continued)

OTHER PUBLICATIONS

Seaborn, Geoffrey E. J. "Clinical Decision Support Algorithm for Prediction of Postoperative Atrial Fibrillation Following Coronary Artery Bypass Grafting." Order No. NS27952 Queen's University (Canada), 2014. Ann Arbor: ProQuest. Web. Oct. 19, 2023. (Year: 2014).*

(Continued)

*Primary Examiner* — Lena Najarian
(74) *Attorney, Agent, or Firm* — Fish & Richardson P.C.

(57) ABSTRACT

This document describes medical systems that use artificial intelligence to facilitate autonomous or semi-autonomous medical procedures. For example, this document describes heart/lung machine systems that are used in conjunction with artificial intelligence systems to facilitate autonomous or semi-autonomous open-heart surgery operations.

13 Claims, 15 Drawing Sheets

(56) References Cited

U.S. PATENT DOCUMENTS

| | | | |
|---|---|---|---|
| 7,364,563 | B2 | 4/2008 | Lucke et al. |
| 7,611,478 | B2 | 11/2009 | Lucke et al. |
| 7,674,235 | B2 | 3/2010 | Nier et al. |
| 7,787,946 | B2 | 8/2010 | Stahmann et al. |
| 7,788,038 | B2 | 8/2010 | Oshita et al. |
| 7,981,281 | B2 | 7/2011 | Yu et al. |
| 8,062,513 | B2 | 11/2011 | Yu et al. |
| 8,862,196 | B2 | 10/2014 | Lynn |
| 8,868,350 | B2 | 10/2014 | Akonur et al. |
| 8,961,461 | B2 | 2/2015 | Stewart et al. |
| 9,002,655 | B2 | 4/2015 | Bernard |
| 9,399,091 | B2 | 7/2016 | Sigg et al. |
| 9,400,199 | B2 | 7/2016 | Wolff |
| 9,486,568 | B2 | 11/2016 | Atallah et al. |
| 9,717,840 | B2 | 8/2017 | Burbank et al. |
| 10,179,199 | B2 | 1/2019 | Bene |
| 10,342,910 | B2 | 7/2019 | Atallah et al. |
| 2002/0068015 | A1 | 6/2002 | Polaschegg et al. |
| 2002/0123905 | A1* | 9/2002 | Goodroe ............... G16H 40/20 705/2 |
| 2002/0169386 | A1 | 11/2002 | Johnson, Jr. |
| 2005/0126961 | A1 | 6/2005 | Bissler et al. |
| 2005/0230314 | A1 | 10/2005 | Kim et al. |
| 2008/0027409 | A1* | 1/2008 | Rudko .................. A61M 5/142 604/503 |
| 2010/0137693 | A1 | 6/2010 | Porras et al. |
| 2016/0256090 | A1 | 9/2016 | Barrett et al. |
| 2018/0060520 | A1* | 3/2018 | Degen .................... G16H 80/00 |
| 2018/0154061 | A1 | 6/2018 | Turner |
| 2018/0361051 | A1 | 12/2018 | Kopperschmidt |
| 2019/0146458 | A1* | 5/2019 | Roh ....................... G16H 30/40 700/98 |
| 2019/0231433 | A1* | 8/2019 | Amanatullah ..... A61B 17/1703 |
| 2019/0365976 | A1 | 12/2019 | Tatonetti |
| 2020/0054816 | A1 | 2/2020 | Frugier |
| 2020/0179045 | A1 | 6/2020 | Levin et al. |
| 2020/0206405 | A1 | 7/2020 | Wyeth et al. |
| 2021/0228794 | A1 | 7/2021 | Lecamwasam et al. |

FOREIGN PATENT DOCUMENTS

| | | | |
|---|---|---|---|
| EP | 1955723 | | 4/2017 |
| EP | 3524290 | | 8/2019 |
| EP | 3145392 | | 10/2019 |
| EP | 3806108 | | 4/2021 |
| WO | WO 2002/49500 | | 6/2002 |
| WO | WO 2002/058536 | | 8/2002 |
| WO | WO 2010/066405 | | 6/2010 |
| WO | WO-2016149794 | A1 * | 9/2016 ........... A61B 5/0022 |
| WO | WO 2019/152699 | | 8/2019 |
| WO | WO 2019/193604 | | 10/2019 |

OTHER PUBLICATIONS

Agarwal et al., "Comparison of closed loop vs. manual administration of propofol using the Bispectral index in cardiac surgery," ACTA Anaesthesiologica Scandinavica, Feb. 2009, 53(3):390-397.

Chen "Automated anesthesia delivery systems in cardiac surgical patients with left ventricular dysfunction: All systems go?" Journal Of Clinical Anesthesia, Nov. 2017, 42:103-105.

Extended European Search Report in European Appln No. 20882513.3, dated Nov. 21, 2022, 12 pages.

Zaouter et al., "The feasibility of a completely automated total IV anesthesia drug delivery system for cardiac surgery," Anesthesia and Analgesia, Oct. 2016, 123(4):885-893.

PCT International Search Report and Written Opinion in International Appln. No. PCT/US2020/058154, dated Dec. 29, 2020, 13 pages.

Amc.nl, [online], "Who is Who in Research," available No. later than Dec. 1, 2019, retrieved on Oct. 26, 2020, retrieved from URL<https://www.amc.nl/web/research-75/department/intensive-care-medicine.htm>, 5 pages.

Arvind et al., "Predicting Surgical Complications in Adult Patients Undergoing Anterior Cervical Discectomy and Fusion Using Machine Learning," Neurospine, 2018, 15(4):329-337.

Baumgartner et al., "A Comprehensive Approach towards Extra-Corporal Circulation Control using Fuzzy Logic," Presented at International Conference on Fuzzy Systems, Barcelona, Spain, Jul. 18- 23, 2010, IEEE, Sep. 2010, 5 pages.

Bidmc.org, [online], "Beth Israel Deaconess Medical Center," 2020, retrieved on Oct. 22, 2020, retrieved from URL<https://www.bidmc.org/>, 5 pages.

Busch et al., "Noninvasive optical measurement of microvascular cerebral hemodynamics and autoregulation in the neonatal ECMO patient," Pediatric Research, 2020, 9 pages.

Campus.uva.nl, [online], "Academic Medical Center," 2020, retrieved on Oct. 23, 2020, retrieved from URL<https://campus.uva.nl/en/amc/academic-medical-center.html?cb>, 3 pages.

Cs.washington.edu, [online], "Investing in the future," 2019, retrieved on Oct. 26, 2020, retrieved from URL<https://www.cs.washington.edu/>, 2 pages.

Dascena.com, [online], "Dascena develops algorithms as predictive biomarkers for complex conditions," 2020, retrieved on Oct. 26, 2020, retrieved from URL<https://www.dascena.com/>, 8 pages.

Dhzb.de, [online], "Welcome to the Department of Cardiothoracic and Vascular Surgery," available no later than Dec. 1, 2019, retrieved on Oct. 26, 2020, retrieved from URL<https://www.dhzb.de/en/departments/cardiothoracic-and-vascular-surgery>, 2 pages.

En.rnhospital.com, [online], "Renmin Hospital of Wuhan University Hubei General Hospital," 2015, retrieved on Oct. 23, 2020, retrieved from URL<http://en.rnhospital.com/contact.html>, 2 pages.

En.umed.wroc.pl, [online], "Department of Anaesthesiology and Intensive Therapy," 2019, retrieved on Oct. 22, 2020, retrieved from URL<https://www.en.umed.wroc.pl/en-anestezjologia>, 1 page.

Fernandes et al., "Machine Learning Models with Preoperative Risk Factors and Intraoperative Hypotension Parameters Predict Mortality After Cardiac Surgery," Journal of Cardiothoracic and Vascular Anesthesia, 2020, 30 pages.

Hatib et al., "Machine-learning Algorithm to Predict Hypotension Based on High-fidelity Arterial Pressure Waveform Analysis," Anesthesiology, 2018, 12 pages.

Health.utah.edu, [online], "Department of Nutrition & Integrative Physiology (NUIP)," 2020, retrieved on Oct. 26, 2020, retrieved from URL<https://health.utah.edu/nutrition-integrative-physiology>, 14 pages.

Icahn.mssm.edu, [online], "Department of Orthopaedics," 2020, retrieved on Oct. 23, 2020, retrieved from URL<https://icahn.mssm.edu/about/departments/orthopaedics>, 2 pages.

Kim et al., "Predicting Cardiac Arrest and Respiratory Failure Using Feasible Artificial Intelligence with Simple Trajectories of Patient Data," J Clin Med, 2019, 8(9):1336, 14 pages.

Lee et al., "Derivation and Validation of Machine Learning Approaches to Predict Acute Kidney Injury after Cardiac Surgery," J Clin Med, 2018, 7(10):322, 13 pages.

Lukaszewski et al., "The use of data science to analyse physiology of oxygen delivery in the extracorporeal circulation," BMC Cardiovascular Disorders, 2019, 19:292, 6 pages.

Lundberg et al., "Explainable machine-learning predictions for the prevention of hypoxaemia during surgery," Nat Biomed Eng., 2018, 2(10):749-760.

Medicine.yonsei.ac.kr, [online], "Dean's Message," 2009, retrieved on Oct. 26, 2020, retrieved from URL<https://medicine.yonsei.ac.kr/en/About_YUCM/message/index.asp>, 1 page.

Meyer et al., "Machine learning for real-time prediction of complications in critical care: a retrospective study," Lancet Respir Med., 2018, 6(12):905-914.

Mohamadlou et al., "Prediction of Acute Kidney Injury With a Machine Learning Algorithm Using Electronic Health Record Data," Can J Kidney Health Dis, 2018, 5:1-9.

Mottchildren.org, [online], "Congenital Heart Center at Mott Children's Hospital," 2020, retrieved on Oct. 23, 2020, retrieved from URL<https://www.mottchildren.org/our-locations/congenital-heart-center-mott-childrens-hospital>, 1 page.

(56) References Cited

OTHER PUBLICATIONS

Nymu-e.ym.edu.tw, [online], "School of Medicine," 2014, retrieved on Oct. 22, 2020, retrieved from URL<https://nymu-e.ym.edu.tw/files/11-1134-18.php>, 2 pages.

Olive et al., "Current monitoring and innovative predictive modeling to improve care in the pediatric cardiac intensive care unit," Translational Pediatrics, 2018, 7(2):120-128.

Peds.us.edu, [online], "Critical Care Medicine," 2020, retrieved on Oct. 23, 2020, retrieved from URL<https://www.peds.uw.edu/specialties/critical-care-medicine>, 2 pages.

Poss et al., "Machine learning reveals serum sphingolipids as cholesterol-independent biomarkers of coronary artery disease," The Journal of Clinical Investigation, 2019, 130(3):1363-1376.

Shah et al., "Neural Networks to Predict Radiographic Brain Injury in Pediatric Patients Treated with Extracorporeal Membrane Oxygenation," Journal of Clinical Medicine, 2020, 9(2718):14 pages.

Shirazu.ac.ir, [online], "Shiraz University," available no later than Dec. 1, 2019, retrieved on Oct. 26, 2020, retrieved from URL<http://www2.shirazu.ac.ir/en>, 1 page.

Tomašev et al., "A clinically applicable approach to continuous prediction of future acute kidney injury," Nature, 2019, 572(7767):116-119.

Tseng et al., "Prediction of the development of acute kidney injury following cardiac surgery by machine learning, " Critical Care, 2020, 24:478, 13 pages.

Ucl.ac.uk, [online], "UCL Computer Science," 2020, retrieved on Oct. 26, 2020, retrieved from URL<https://www.ucl.ac.uk/computer-science>, 5 pages.

Uclahealthy.org, [online], "UCLA Anesthesiology & Perioperative Medicine," 2020, retrieved on Oct. 26, 2020, retrieved from URL<https://www.uclahealth.org/anes/>, 3 pages.

Utsouthwestern.edu, [online], "UTSouthwestern Medical Center," 2020, retrieved on Oct. 23, 2020, retrieved from URL<https://www.utsouthwestern.edu/>, 4 pages.

Wijnberge et al., "Effect of a Machine Learning-Derived Early Warning System for Intraoperative Hypotension vs Standard Care on Depth and Duration of Intraoperative Hypotension During Elective Noncardiac Surgery: The HYPE Randomized Clinical Trial," JAMA, 2020, 323(11):1052-1060, E1-E9.

Wijnberge et al., "The use of a machine-learning algorithm that predicts hypotension during surgery in combination with personalized treatment guidance: study protocol for a randomized clinical trial, " Trials, 2019, 20:582, 9 pages.

Xsensor.com, [online], "New Wave of Innovation: AI/ML in Medtech," 2020, retrieved on Oct. 26, 2020, retrieved from URL<https://www.xsensor.com/post/new-wave-of-innovation-ai-ml-in-medtech>, 4 pages.

Xsensor.com, [online], "Optimize Human Performance," 2020, retrieved on Oct. 26, 2020, retrieved from URL<https://www.xsensor.com/>, 3 pages.

Zhang et al., "Continuous perfusion of donor hearts with oxygenated blood cardioplegia improves graft function," Transplant International: Official Journal of the European Society for Organ Transplantation, 2010, 23(11):1164-1170.

PCT International Preliminary Report on Patentability in International Appln. No. PCT/US2020/058154, dated May 3, 2022, 11 pages.

\* cited by examiner

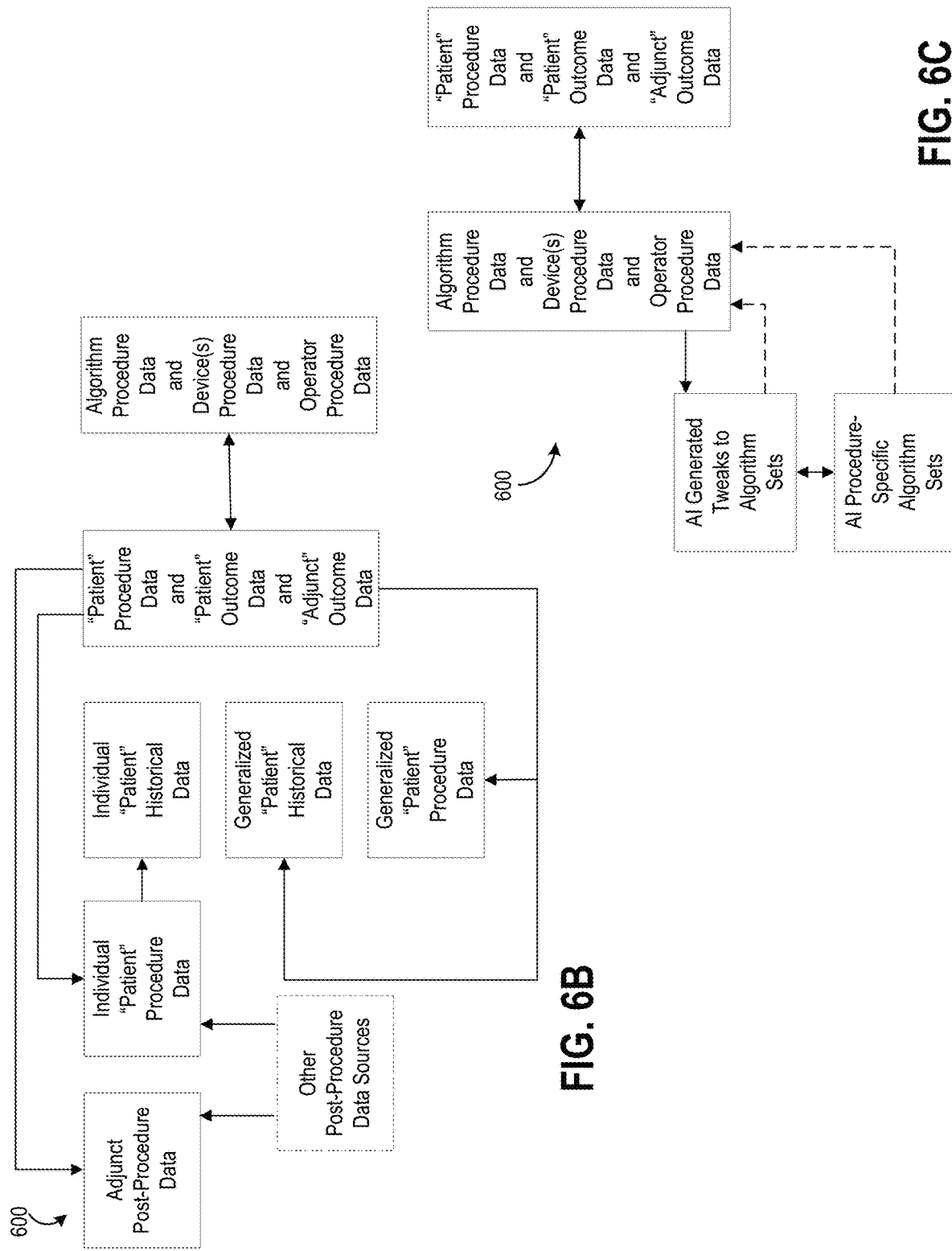

SEMI-AUTONOMOUS MEDICAL SYSTEMS AND METHODS

CROSS-REFERENCE TO RELATED APPLICATIONS

This application claims the benefit of U.S. Provisional Application Ser. No. 62/929,134, filed Nov. 1, 2019. The disclosure of the prior application is considered part of (and is incorporated by reference in) the disclosure of this application.

BACKGROUND

1. Technical Field

This document relates to medical systems that use artificial intelligence to facilitate autonomous or semi-autonomous medical treatment procedures. For example, this document relates to heart/lung machine systems that use artificial intelligence to facilitate autonomous or semi-autonomous open-heart surgeries.

2. Background Information

Artificial intelligence (AI), sometimes referred to as machine intelligence, is intelligence demonstrated by machines and systems of machines. The term "artificial intelligence" is often used to describe machines (or computers) that mimic "cognitive" functions that humans associate with the human mind, such as "learning" and "problem solving."

Autonomous operations is the ability of a system to sense the state of its environment, analyze the data it senses to find operational problems or changing resource demands, and adapt the environment dynamically to resolve.

Heart/lung machine systems are used, along with an extracorporeal circuit and hollow fiber oxygenator, to meet a patient's circulatory and blood gas exchange needs during medical procedures such as cardiopulmonary bypass surgery. Blood from the patient is either gravity drained, or VAVD (vacuum assisted venous drainage) is used, to obtain the required amount of flow to maintain sufficient volume in a reservoir of the extracorporeal circuit. A pump, such as a peristaltic pump or a centrifugal pump coupled with a magnetic drive system, is sometimes used in the main line of the extracorporeal circuit in order to pump blood from the reservoir, through the oxygenator, and finally back to the patient. In addition to a heart/lung machine per se, heart-lung machine systems can include multiple types of patient monitoring devices that are used in conjunction with the heart/lung machine.

SUMMARY

This document describes medical systems that use artificial intelligence to facilitate autonomous or semi-autonomous medical treatment procedures using a medical treatment system in conjunction with other devices/systems. For example, this document describes heart/lung machine systems that are used in conjunction with artificial intelligence computer systems to facilitate autonomous or semi-autonomous open-heart surgeries.

In one aspect, this disclosure is directed to a system for performing an open-heart surgical procedure on a patient. The system includes a heart/lung machine, one or more monitoring devices, a database, and a computing system. The one or more monitoring devices are configured to monitor parameters indicative of conditions of the patient during the procedure. The database stores: (1) first medical data describing one or more conditions of the patient; (2) second medical data that summarizes health information of a general population of other patients; and (3) third medical data defining target ranges for operational parameters of the heart/lung machine and the one or more monitoring devices during the procedure. The computer system is configured to receive in real-time during the procedure: (a) operational data from the heart/lung machine; (b) the parameters from the one or more monitoring devices; (c) the first medical data; (d) the second medical data; and (e) the third medical data. The computer system is further configured to, during the procedure, iteratively analyze: (i) the operational data from the heart/lung machine, (ii) the parameters from the one or more monitoring devices, (iii) the first medical data, and (iv) the second medical data. The computer system is further configured to, during the procedure, iteratively determine predictions, based on a comparison of the analysis of (i)-(iv) to the third medical data, that the operational data from the heart/lung machine or the parameters from the one or more monitoring devices are trending out of the target ranges.

Such a system for performing an open-heart surgical procedure on a patient may optionally include one or more of the following features. The computer system may be further configured to generate, based on the predictions, a trained model for the procedure. In some embodiments, generating the trained model for the procedure comprises iteratively training a model for the procedure by correlating each of the predictions to (i) the operational data from the heart/lung machine, (ii) the parameters from the one or more monitoring devices, (iii) the first medical data, and (iv) the second medical data across one or more model layers using one or more machine learning algorithms. The trained model may be stored in the database. The computer system may also be configured to determine predictions that the operational data from the heart/lung machine or the parameters from the one or more monitoring devices are trending out of the target ranges based on applying the trained model for the procedure. In some embodiments, the computer system is further configured to generate, based on the predictions, recommended adjustments to be made in real-time during the procedure to at least one of the heart/lung machine or the one or more monitoring devices. The computer system may also be further configured to, in real-time during the procedure, select one or more of the recommended adjustments based at least in part on analyzing (i) the operational data from the heart/lung machine, (ii) the parameters from the one or more monitoring devices, (iii) the first medical data, and (iv) the second medical data. The computer system may also be further configured to, in real-time during the procedure, autonomously implement the selected one or more recommended adjustments. In some embodiments, the computer system is further configured to generate, based on autonomously implementing the selected one or more recommended adjustments, a trained model for recommending procedure adjustments. The computer system may be further configured to receive operational data from a plurality of heart/lung machines. In some cases, the one or more monitoring devices include at least one of a camera or a sensor array. The one or more monitoring devices may also include a urine collection bag monitor. The first medical data may include current conditions of the patient and historic conditions of the patient. The second medical data may include historical health information of patients who have undergone the procedure.

In another aspect, this disclosure is directed to a computer-implemented method for use while performing an open-heart surgical procedure on a patient. The method includes receiving, by a computer system and in real-time during the procedure: (i) operational data from a heart/lung machine, (ii) parameters indicative of conditions of the patient during the procedure from one or more monitoring devices, (iii) first medical data describing one or more conditions of the patient, (iv) second medical data that summarizes health information of a general population of other patients, and (v) third medical data defining target ranges for operational parameters of the heart/lung machine and the one or more monitoring devices during the procedure. The method also includes iteratively analyzing, by the computer system and during the procedure, (i)-(iv). The method also includes determining predictions, based on a comparison of the analysis of (i)-(iv) to the third medical data, that the operational data from the heart/lung machine or the parameters from the one or more monitoring devices are trending out of the target ranges.

Such a computer-implemented method for use while performing an open-heart surgical procedure on a patient may optionally include one or more of the following features. The method may also include generating, based on the predictions, a trained model for the procedure. Generating the trained model for the procedure may include iteratively training a model for the procedure by correlating each of the predictions to (i) the operational data from the heart/lung machine, (ii) the parameters from the one or more monitoring devices, (iii) the first medical data, and (iv) the second medical data across one or more model layers using one or more machine learning algorithms. The method may also include determining predictions that the operational data from the heart/lung machine or the parameters from the one or more monitoring devices are trending out of the target ranges based on applying the trained model for the procedure.

In another aspect, this disclosure is directed to a system for performing a medical procedure on a patient. The system includes a medical treatment system, one or more monitoring devices, a database, and a computing system. The one or more monitoring devices are configured to monitor parameters indicative of conditions of the patient during the procedure. The database stores: (1) first medical data describing one or more conditions of the patient; (2) second medical data that summarizes health information of a general population of other patients; and (3) third medical data defining target ranges for operational parameters of the medical treatment system and the one or more monitoring devices during the procedure. The computer system is configured to receive in real-time during the procedure: (a) operational data from the medical treatment system; (b) the parameters from the one or more monitoring devices; (c) the first medical data; (d) the second medical data; and (e) the third medical data. The computer system is further configured to, during the procedure, iteratively analyze: (i) the operational data from the medical treatment system, (ii) the parameters from the one or more monitoring devices, (iii) the first medical data, and (iv) the second medical data. The computer system is further configured to, during the procedure, iteratively determine predictions, based on a comparison of the analysis of (i)-(iv) to the third medical data, that the operational data from the medical treatment system or the parameters from the one or more monitoring devices are trending out of the target ranges.

Such a medical treatment system may optionally include one or more of the following features. The computer system may also be configured to generate, based on the predictions, recommended adjustments to be made in real-time during the procedure to at least one of the medical treatment system or the one or more monitoring devices. The computer system may also be configured to, in real-time during the procedure: (A) select one or more of the recommended adjustments based at least in part on analyzing (i) the operational data from the medical treatment system, (ii) the parameters from the one or more monitoring devices, (iii) the first medical data, and (iv) the second medical data; and (B) autonomously implement the selected one or more recommended adjustments.

The technology described in this document can be used to provide multiple advantages and benefits. For example, techniques used to assist clinicians in determining medical procedure adjustments that ensure patient health and safety during a medical procedure are improved by the systems and methods described herein. As described herein, the need for medical procedure adjustments can be accurately predicted and timely provided to a clinician, such as a perfusionist, during a medical procedure. For example, in some cases the clinician can be alerted to a potential of harm to the patient such that the clinician can deal with and avoid the harm before it occurs. This saves the clinician from having to spend critical time during the procedure to make all such determinations. This can also mitigate the possibility of human error in making such determinations during the stresses of the procedure. Patient safety and procedure outcomes can be improved for these reasons.

The disclosed technology can also enhance information processing to provide benefits to patients and care providers. A single person's ability to analyze extensive and complex data about a patient and general population of patients is limited. Moreover, it is possible the human analysis can miss pertinent pieces of data that can otherwise be used to assess accurately a patient's conditions during a procedure. The technology described herein can overcome these challenges by providing a technological means to understand and analyze thousands of data and provide for predictive trends and analysis regarding a patient's safety before, during, and after medical procedures. Moreover, the technology makes it possible to incorporate data from a wide variety of sources, such as databases, patient monitoring devices, and sensors, to generate robust and accurate trends and predictions. Machine learning can be incorporated into the disclosed technology to continuously improve trend analysis, predictions of patient outcomes and safety, and generation of procedure adjustment recommendations. Continuous improvements are advantageous to ensure that the disclosed system can predict patient conditions during any type of medical procedure.

Moreover, labor costs can be reduced using the systems and methods described herein. For example, in some cases the labor costs for perfusionists who control a heart/lung machine during open-heart surgeries can be reduced, as described below. Medical procedure adjustment recommendations and decisions can be made with the assistance of this technology, which can reduce the need for a perfusionist to be dedicated to a single procedure, control medical devices, perform procedural adjustments, and make decisions about what adjustments are needed to ensure the patient's safety. Instead, in some cases a practitioner such as a perfusionist can oversee multiple procedures at once from a central location, and accept decisions and/or recommendations that are generated by the disclosed technology in reference to each of the multiple procedures. The disclosed technology can enhance the practitioner's proficiency in addressing issues that arise during the procedure. The disclosed technology can provide for two-way communication with medical devices used during the procedure such that, in some cases, medical procedure adjustments can be implemented remotely and/or autonomously. These procedure adjustments can also be presented or suggested to the practitioner, and the practitioner can make the actual decision regarding whether or not to implement the proposed procedure adjustments.

The disclosed technology can optionally provide for semi-autonomous control of multiple devices that are used during a medical procedure. Artificial intelligence (AI), data integration, and deep learning (DL), make accurate semi-autonomous control possible. As a result of employing such techniques, patients may be discharged sooner and experience fewer complications during the procedure and recovery.

The costs of medical procedures can also be reduced for a variety of reasons. First, fewer practitioners can be hired since one practitioner can oversee multiple procedures at a time. Second, the practitioner can focus on performing the medical procedure without having to divert their attention to monitoring device and patient conditions. Third, human error in diagnosing and addressing issues during the procedure can be greatly reduced and/or eliminated.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. In case of conflict, the present specification, including definitions, will control. In addition, the materials, methods, and examples are illustrative only and not intended to be limiting. Furthermore, all references to features or objects A-N mean that there can be an infinite number of such features or objects.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

FIGS. 6A-6C are flowcharts of an example process to improve predicting patient conditions after a semi-autonomous medical procedure is completed.

Like reference numbers represent corresponding parts throughout.

DETAILED DESCRIPTION

This document describes medical systems that use artificial intelligence to facilitate autonomous and/or semi-autonomous medical treatment procedures using a medical treatment system in conjunction with other devices/systems. For example, this document describes heart/lung machine systems that use artificial intelligence to facilitate autonomous or semi-autonomous open-heart surgery open-heart surgeries. This document also describes heart/lung machine systems that use artificial intelligence to facilitate manual performance of open-heart surgery operations.

While the systems provided herein for performing a semi-autonomous medical procedure on a patient are primarily described in the context of an open-heart surgery procedure using a heart/lung bypass machine, it should be understood that the open-heart surgery procedure using a heart/lung bypass machine is just an example. The innovative concepts described in the context of the open-heart surgery procedure using a heart/lung bypass machine extend without limitation to various other types of medical procedures using medical treatment systems in conjunction with other devices/systems.

Figure 1:
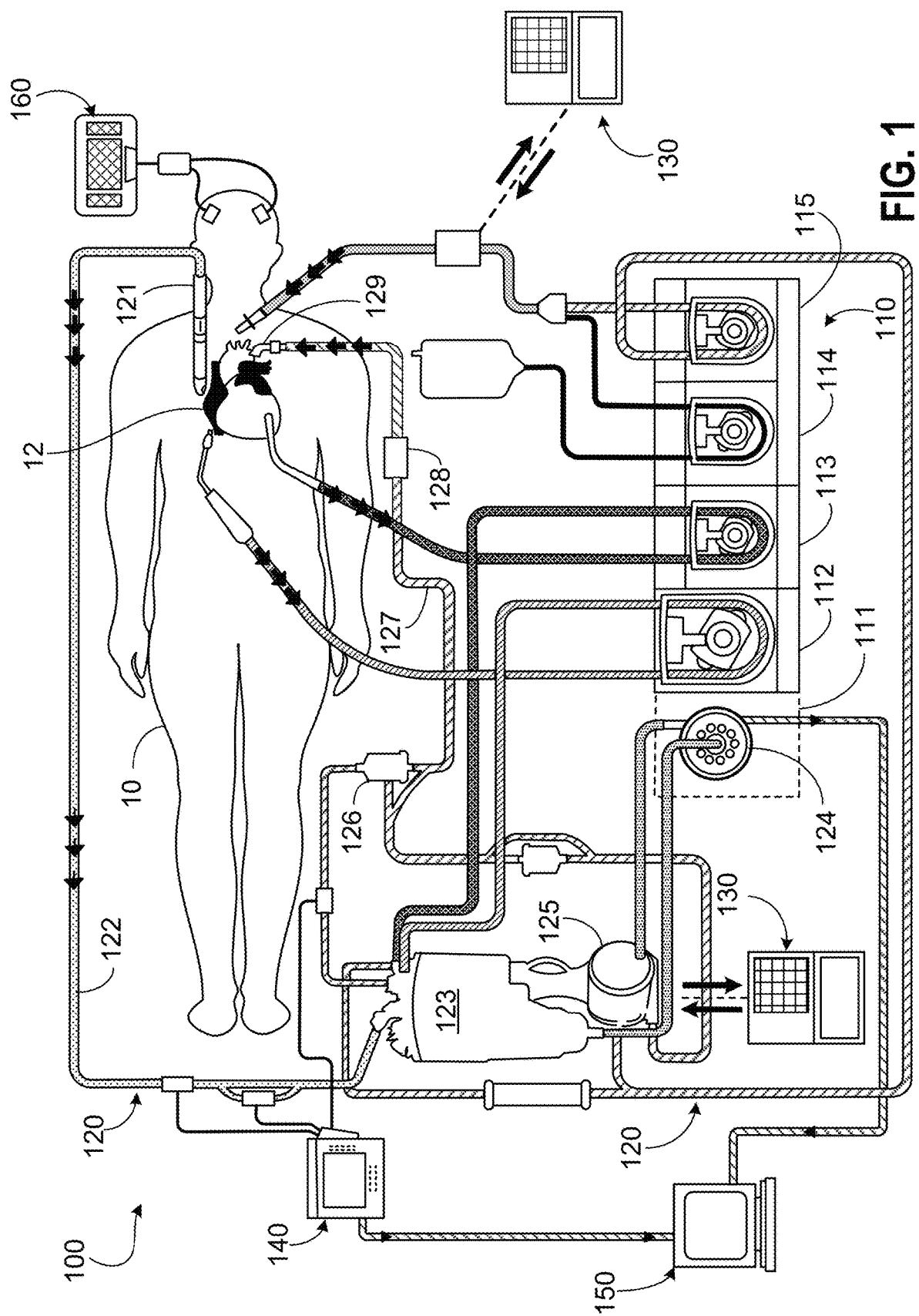
FIG. 1 is a schematic diagram of a patient undergoing open-heart surgery while being supported using a conventional heart/lung machine system and extracorporeal circuit.

As shown in FIG. 1, various types of medical procedures can be performed on a patient 10 while the patient 10 is connected to a life-sustaining heart/lung bypass machine system 100. In this example, the patient 10 is undergoing open-heart surgery during which the heart 12 and lungs of the patient 10 are temporarily intentionally caused to cease functioning. Because the body of the patient 10 continues to have a metabolic need to receive a supply of circulating oxygenated blood during the medical procedure, however, the heart/lung bypass machine system 100 performs such functions. That is, as described further below, the heart/lung bypass machine system 100 is connected to the patient 10 and performs the functions of the heart 12 and lungs of the patient 10 so that the patient 10 stays alive and healthy during open-heart surgery.

The heart/lung bypass machine system 100 can be used for many different types of medical procedures. For example, the medical procedures for which the heart/lung bypass machine system 100 can be used include, but are not limited to, coronary artery bypass grafts, heart valve repairs, heart valve replacements, heart transplants, lung transplants, ablation procedures, repair of septal defects, repair of congenital heart defects, repair of aneurysms, pulmonary endarterectomy, pulmonary thrombectomy, and the like.

The heart/lung bypass machine system 100 is typically set up and operated by a specially-trained clinician/practitioner called a perfusionist. Perfusionists form part of the wider cardiovascular surgical team that includes cardiac surgeons, anesthesiologists, and nurses. During medical procedures using the heart/lung bypass machine system 100, the perfusionist is tasked with many responsibilities, not the least of which is ensuring that the patient 10 is kept alive and healthy by operating the heart/lung bypass machine system 100 in a manner that maintains blood flow to the patient's tissues, and which regulates levels of oxygen and carbon dioxide in the blood of the patient 10. Other responsibilities of the perfusionist include, but are not limited to, administering blood products, administering anesthetic agents or drugs, measuring selected laboratory values (such as blood cell count), monitoring circulation, monitoring blood gases, surveilling anticoagulation, induction of hypothermia, and hemodilution. The responsibilities of the perfusionist are diverse, dynamic, and critically important to achieving successful outcomes of procedures performed on the patient 10 using the heart/lung bypass machine system 100.

In the depicted example, the heart/lung bypass machine system 100 includes components and sub-systems such as a heart/lung machine 110, an extracorporeal circuit 120, one or more temperature control systems 130, a blood monitoring system 140, a perfusion data management system 150, and a regional oximetry system 160. Some types of procedures that use the heart/lung bypass machine system 100 may not require all of the components and sub-systems that are shown. Some types of procedures that use the heart/lung bypass machine system 100 may require additional components, monitors, and/or sub-systems that are not shown.

The extracorporeal circuit 120 is connected to the patient 10, and to the heart/lung machine 110. Other systems, such as the temperature control system 130, blood monitoring system 140 (e.g., a CDI® blood gas monitor made by Terumo Cardiovascular Corporation), and perfusion data management system 150 may also be arranged to interface with the extracorporeal circuit 120. The extracorporeal circuit 120 is connected to the patient 10 at the patient's heart 12. Oxygen-depleted blood (venous blood) from the patient 10 is extracted from the patient 10 at the patient's heart 12 using a venous catheter 121. As described further below, the blood is circulated through the extracorporeal circuit 120 to receive oxygen and remove carbon dioxide. The oxygenated blood is then returned through the extracorporeal circuit 120 to the patient's heart 12 via an aortic cannula 129.

The extracorporeal circuit 120 can include, at least, a venous tube 122 (e.g., lining, tubing) that is coupled to the venous catheter 121, a blood reservoir 123, a centrifugal pump 124, an oxygenator 125, an arterial filter 126, one or more air bubble detectors 128, and an arterial tube 127 (e.g., lining, tubing) that is coupled to the aortic cannula 129. The venous catheter 121 and venous tube 122 are in fluid communication with the venous side of the circulatory system of the patient 10. The venous tube 122 is also in fluid communication with an inlet to the reservoir 123. An outlet from the reservoir 123 is connected by tubing to an inlet of the pump 124. The outlet of the pump 124 is connected by tubing to an inlet of the oxygenator 125. The outlet of the oxygenator 125 is connected by tubing to an inlet of the arterial filter 126. An outlet of the arterial filter 126 is connected to the arterial tube 127. One or more pressure transducers (not depicted) can be located along the arterial tube 127 to detect a heart/lung machine (HLM) system line pressure of the blood in the arterial tube 127, which is measured by the heart/lung machine 110 and monitored by the perfusionist. The arterial tube 127 is connected to the arterial cannula 129, which is in physical contact with the heart 12 and in fluid communication with the arterial side of the circulatory system of the patient 10.

Briefly, the extracorporeal circuit 120 operates by removing venous, oxygen-depleted blood from the patient 10 via the venous catheter 121, and depositing the venous blood in the reservoir 123 via the venous tube 122. In some cases, gravity is used to cause the blood to flow or drain from the patient 10 to the reservoir 123. In some cases, vacuum is used to assist the blood to flow from the patient 10 to the reservoir 123. At least some amount of blood is intended to be maintained in the reservoir 123 at all times during the surgical procedure. Otherwise, if the reservoir 123 becomes empty, air could be pumped into the extracorporeal circuit 120, and potentially into the vasculature of the patient 10. Such a result would likely be catastrophic for the patient 10. Accordingly, the perfusionist is tasked with visually monitoring the level of the blood in the reservoir 123. In addition, level detectors (not depicted) can be included in conjunction with the reservoir 123 to issue an alarm in response to detection of low-level conditions within the reservoir 123. Moreover, one or more air bubble detectors 128 can be located at various sites along the extracorporeal circuit 120. Blood from the reservoir 123 is drawn from the reservoir 123 by the pump 124. While the depicted embodiment includes a one-time use centrifugal pump as the pump 124, in some cases a peristaltic pump of the heart/lung machine 110 is used instead. The pressure generated by the pump 124 propels the blood through the oxygenator 125. The perfusionist will adjust the pump 124 to operate as desired, while avoiding operational issues such as negative cavitation that could create micro air in the blood of the extracorporeal circuit 120. In the oxygenator 125, the venous blood is enriched with oxygen, and carbon dioxide is removed from the blood. The now oxygen-rich arterial blood exits the oxygenator 125, travels through the arterial filter 126 to remove emboli, and is injected into the patient's heart 12 through the arterial tube 127 via the aortic cannula 129. The extracorporeal circuit 120 can also include tubing and other components for facilitating functions such as, but not limited to, drainage of blood accumulating in the heart of the patient 10, providing surgical suction for maintaining visibility of the surgical field, delivery of cardioplegia solution to facilitate myocardial protection of the heart 12 for the patient 10 during the procedure, measuring blood parameters, removing air from the blood, hemoconcentration, drug addition, obtaining blood samples, heating and cooling of the blood, and the like.

During a surgical procedure using the heart/lung bypass machine system 100, various vital signs of the patient 10 are measured and/or monitored. For example, a patient mean arterial pressure ("MAP") may be measured. The MAP of the patient 10 is a parameter that a perfusionist operating the heart/lung bypass machine system 100 will monitor in order to ensure that the heart/lung bypass machine system 100 is functioning as desired during the surgical procedure. In some cases, the MAP reading is displayed on a screen of an anesthesia system, and/or displayed on the operating room screen. If the MAP of the patient 10 is outside of a desired range, the perfusionist may make adjustments to the heart/lung bypass machine system 100 to improve the MAP of the patient 10.

The heart/lung bypass machine system 100 also includes the heart/lung machine 110. The heart/lung machine 110 is a complex system that includes multiple pumps, monitors, controls, user interfaces, alarms, safety devices, and the like, that are all monitored and operated/adjusted by the perfusionist during a surgical procedure. For example, the depicted heart/lung machine 110 includes an arterial pump 111 (which can be a drive system for a disposable centrifugal pump 124 as shown, or a peristaltic pump), a suction pump 112, a vent/drainage pump 113, a cardioplegia solution pump 114, and a cardioplegia delivery pump 115. The heart/lung machine 110 can also include, or be interfaced with, devices such as a tubing occluder, gas blender, and the like. The operational parameters of the heart/lung machine 110, such as the rotational speed and other parameters of each of the pumps, are set and adjusted by the perfusionist. For example, the speed of the arterial pump 111 is adjusted to maintain a desirable level of blood in the reservoir 123, and to provide a requisite level of blood circulation within the patient 10.

The heart/lung bypass machine system 100 also includes one or more temperature control systems 130. In a first aspect, the temperature control system(s) 130 is/are used to heat and cool the patient's blood in the oxygenator 125 via a heat exchanger. Additionally, the temperature control system(s) 130 is/are used to heat and cool the cardioplegia solution being delivered to the heart 12 of the patient 10. In general, the temperature control system(s) 130 is/are used in cooling modes during the procedure (to reduce metabolic demands), and subsequently used to warm the blood and/or cardioplegia solution when the surgical procedure is nearing its end. The perfusionist is tasked with monitoring and adjusting the temperature control system(s) 130 as needed during the surgical procedure.

The heart/lung bypass machine system 100, as depicted, also includes the blood monitoring system 140. The blood monitoring system 140 is used to monitor the extracorporeal blood of the patient 10 during the surgical procedure. Parameters being monitored can include, but are not limited to, pH, $pCO_2$, $pO_2$, K+, temperature, $SO_2$, hematocrit, hemoglobin, base excess, bicarbonate, oxygen consumption and oxygen delivery. The perfusionist is tasked with monitoring the blood monitoring system 140 during the surgical procedure. In some cases, the perfusionist will need to adjust other components or subsystems of the heart/lung bypass machine system 100 in response to readings from the blood monitoring system 140.

The heart/lung bypass machine system 100, as depicted, also includes the perfusion data management system 150 and the regional oximetry system 160. These systems can also be used by the perfusionist to monitor the status of the patient 10 and/or the status of the heart/lung bypass machine system 100 during surgical procedures.

From the above description, it can be observed and understood that the perfusionist is tasked with a vast amount of very important responsibilities during a surgical procedure using the heart/lung bypass machine system 100. The provision of assistance to the perfusionist by systems using artificial intelligence to facilitate autonomous or semi-autonomous operations could be very beneficial.

Figure 2A:
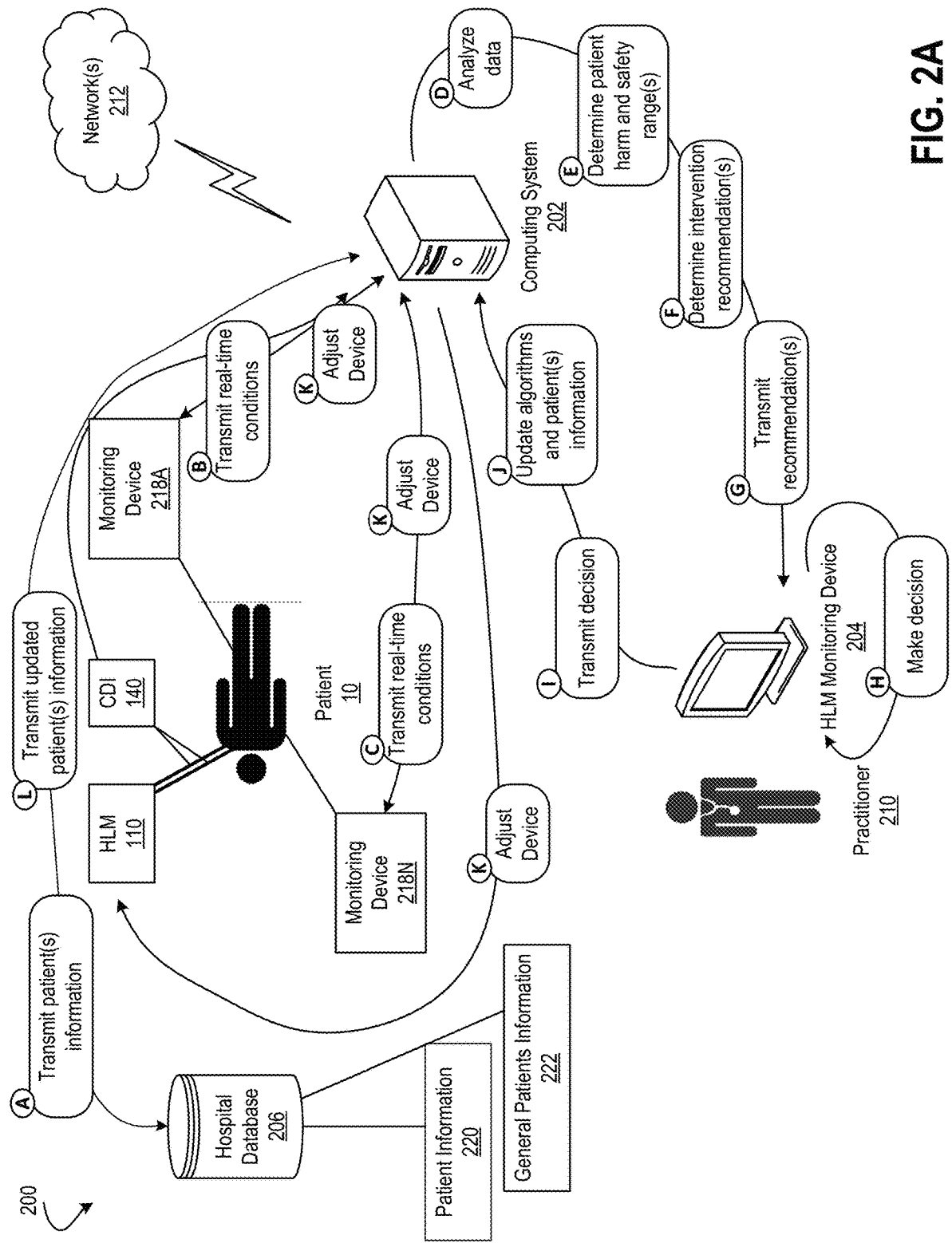
FIGS. 2A-2B are schematic diagrams of an example system used to perform a semi-autonomous medical procedure.

Referring also to FIG. 2A, an example computing system 202 (or "computer system") can be used to perform a semi-autonomous medical procedure 200. The medical procedure 200 can include a practitioner 210 (e.g., perfusionist or other type of clinician) and the patient 10. The computing system 202 can be in communication (e.g., wired and/or wireless) with a heart-lung bypass machine (HLM 110) monitoring device 204, a hospital database 206, one or more monitoring devices 218A-N, and the blood monitoring system 140 (e.g., CDI® blood gas monitor). Wired and/or wireless communication can be provided via network(s) 212. The monitoring device 204 can display information about the HLM 110 and other devices/systems.

In some implementations, the monitoring devices 218A-N can include the regional oximetry system 160 and/or the perfusion data management system 150, as described in reference to FIG. 1. The monitoring devices 218A-N can be configured to monitor real-time conditions of the patient 10 and/or extracorporeal circuit 120 during the medical procedure 200. The monitoring devices 218A-N can be different types of monitoring system and can include sensors and/or sensor arrays. The monitoring devices 218A-N can also be, or comprise, one or more cameras or other optical sensors. In some embodiments, the cameras can look at device displays and capture content displayed on the device displays. The content can be interpreted and reported to the computing system 202 for use in further analysis, including to generate recommended procedural adjustments in real-time during the procedure 200. In yet other embodiments, the monitoring devices 218A-N can be devices that are not connected to the patient 10. Such devices 218A-N can include sensors configured to monitor conditions of an environment of the patient 10. For example, the devices 218A-N can monitor a room temperature and/or a room humidity level.

The computing system 202 can request and receive from the hospital database 206 patient information (A). The hospital database 206 can store patient information 220 and general patients information 222. The patient information 220 can be specific to the particular patient 10 who is undergoing the medical procedure 200. For example, the patient information 220 can include historic information about the patient 10 during previous procedures, health conditions, vitals, etc. The general patients information 222 can include anonymized information about patients who, for example, have undergone similar procedures as the medical procedure 200. The information 222 can also include anonymized information about patients who have similar conditions (e.g., age, gender, health issues, etc.) and/or vitals as the patient 10. Moreover, the information 222 can include anonymized, general trends about patients. The computing system 202 can use the patient specific information 220 and the general patients information 222 to perform more robust analysis on conditions that the patient 10 experiences before, during, and after the procedure 200. This information can be beneficial to predict more accurately the potential for benefits and harms to the patient 10. This information can also be beneficial to generate procedure adjustment recommendations that prevent predicted harms from occurring and that optimize control adjustments and settings.

The computing system 202 can also automatically receive real-time conditions of the patient 10 from the monitoring devices 218A-N and/or the blood monitoring system 140 in B-C. The computing system 202 can also automatically receive real-time operational data (e.g., parameters, conditions, feedback, readings, etc.) from one or more devices used during the procedure, such as from the monitoring devices 218A-N and/or the blood monitoring system 140. In some implementations, the real-time conditions and patient(s) information can be received simultaneously at the computing system 202. In other implementations, the real-time conditions and patient(s) information can be received at different times (e.g., the computing system 202 can request the information and/or conditions at different times). For example, the computing system 202 can request the patients information 220 and 222 before the procedure 200. The system 202 can use this requested information to predict patient conditions during the procedure 200. The system 202 can also use this information to generate medical procedure adjustment recommendations.

During the procedure 200, the computing system 202 can request the real-time conditions from the monitoring devices 218A-N and/or the blood monitoring system 140 to confirm the predictions made before the procedure 200 began. The system can then make any necessary modifications or updates to the medical procedure adjustment recommendations. After the procedure 200, the computing system 202 can request the patients information 220 and 222 and real-time conditions to predict how the patient is going to recover. The predictions can also be used to propose therapies, treatments, and the like to accelerate and/or ensure better recovery of the patient. In other examples, the computing system 202 can continuously receive information from the database 206, the monitoring devices 218A-N, and the blood monitoring system 140 before, during, and/or after the procedure 200.

Still referring to FIG. 2A, once the computing system 202 receives patient(s) information and/or real-time conditions in A-C, the system 202 can analyze the data in D. Artificial intelligence (AI), machine learning (ML), deep learning (DL), and/or other algorithms and models can be used by the computing system 202 to predict trends in patient conditions and parameters from one or more of the monitoring devices 218A-N and/or the blood monitoring system 140. For example, the computing system 202 can, during the procedure, iteratively analyze operational data from the blood monitoring system 140 (e.g., heart/lung machine), parameters from the one or more monitoring devices 218A-N, patient information 220 (e.g., "first medical data"), and general patient information 222 (e.g., "second medical data"). The computing system 202 can then determine predictions, based on the analysis of the above-mentioned to data defining target ranges for operational parameters of the blood monitoring system 140 and the one or more monitoring devices 218A-N during the procedure, that the operational data from the blood monitoring system 40 or the parameters from the one or more monitoring devices 218A-N are trending out of the target ranges. These techniques can also be used to determine procedure adjustments that can maintain the patient 10's safety before, during, and/or after the procedure 200 as well as maintain one or more parameters of the blood monitoring system 140 and/or the one or more monitoring devices 218A-N.

In some embodiments, analyzing the data can be performed at a remote location from the procedure 200. In some examples, the computing system 202 can be a central server system that performs all analytics for various medical procedures (e.g., refer to FIG. 2B). The central server can be at a location remote from one or more of the medical procedures. In other examples, the computing system 202 can be at the location of the procedure 200 and in communication with one or more other computing systems at different locations. The system 202 can run algorithms or models specific to a particular device that is used during the procedure 200, such as the HLM 110. The system 202 can then communicate with one or more other computing systems that run other algorithms or models specific to other devices. As a result, more robust predictions and analysis can be performed through this decentralized framework.

Based on analyzing the data from multiple sources, the system 202 can determine and/or predict potential harm to the patient 10 as well as one or more safety ranges in E. As mentioned, E can be performed before, during, and/or after the procedure 200. The safety ranges can be determined for each parameter monitored by the devices 218A-N and the HLM 110. As described further in reference to FIGS. 7A-7D, during the procedure 200, it is important to maintain each parameter in associated safety ranges. Monitoring and maintaining each parameter can improve an overall condition and safety of the patient 10. If a parameter escapes a determined safety range for that parameter, then some level of action (e.g., adjustment) may be required. More stringent and/or urgent adjustments can be generated and required based on how much a parameter exceeds, or is expected to exceed, the associated safety range. The safety range for each parameter can be determined based on real-time conditions received in B and C as well as patient information received in A.

The system 202 can then determine procedure adjustment recommendations in F and transmit the recommendations to the HLM monitoring device 204 in G. The procedure adjustment recommendations can include recommended changes to one or more of the monitoring devices 218A-N. These recommendations can be generated based on how much a particular parameter being monitored exceeds or is expected to exceed the parameter's safety range. These recommendations can also be generated based on an overall real-time and/or predicted condition of the patient 10.

The practitioner 210 can make a decision (H) about whether to perform one or more of the recommendations. In some embodiments, the practitioner 210 can select one or more of the recommendations on a user interface of the HLM monitoring device 204. In some implementations (e.g., medical procedure in which the patient is put into serious harm that requires immediate procedure adjustment), the computing system 202 can transmit a determined procedure adjustment to the HLM monitoring device 204 and/or one or more monitoring devices 218A-N and then automatically perform the determined procedure adjustment without input or review from the practitioner 210. The computing system 202 can also notify the practitioner 210 of the procedure adjustment as it is being automatically and/or autonomously performed. This can be beneficial in situations where one or more parameters (e.g., operational parameters) are exceeding or expect to exceed upper limits of the determined safety ranges (e.g., refer to FIGS. 7A-7D). If one or more parameters are reaching the upper limits, then immediate action can be required to bring the parameters back into the safety ranges. Otherwise, if the parameters are not immediately adjusted, the overall condition and/or health of the patient can be at risk. Whether the practitioner 210 makes a selection or the system 202 automatically performs the procedure adjustment, the practitioner 210 can maintain operational control of the procedure 200. The practitioner 210's skills and expertise are not compromised—instead, the practitioner 210 can focus on other tasks that may arise during the procedure 200. In some embodiments, the practitioner 210 may be required to perform a manual adjustment to one or more of the monitoring devices 218A-N. For example, a kink in a tube cannot be fixed automatically by the system 202. As a result, the practitioner 210 can be prompted to immediately fix the kinking in the tube. An urgency to fix the kinking can be determined based on how close or how much the associated parameters exceed the upper limits of their safety ranges.

In I, the practitioner 210's selection of a procedure adjustment recommendation can be transmitted from the HLM monitoring device 204 to the computing system 202. The computing system 202 can update algorithm(s) and/or model(s) that the system 202 uses to determine patient harm and safety range(s) (E) and procedure adjustment recommendations (F) based on the practitioner 210's decision (J). For example, in some embodiments, the system 202 can generate, based on the predicted procedure adjustment recommendations and the practitioner 210's selection of any one of the recommendations, a trained model for the procedure. The trained model can be a deep learning model. Generating the trained model for the procedure can include iteratively training a model for the procedure by correlating each of the predictions to operational data from the blood monitoring system 140 (e.g., HLM), parameters from the one or more monitoring devices 218A-N, patient information 220 (e.g., first medical data), and general patients information 222 (e.g., second medical data) across one or more model layers using one or more machine learning algorithms. The trained model can also be stored in a database. One or more other trained models can be generated. For example, the system 202 can generate, based on autonomously implemented the practitioner 210's selection of one or more procedure adjustment recommendations, a trained model for recommending procedure adjustments.

Additionally, as described throughout this disclosure, the system 202 can also determine predictions that the operational data from the blood monitoring system 140 or the parameters from the one or more monitoring devices 218A-N are trending out of their respective target (e.g., safety, ideal) ranges based on applying the trained model for the procedure. As a result of generating such trained models and using them during analysis, the computing system 202 can more accurately predict conditions to ensure patient safety and improve procedure outcomes. The system 202 can also update information about the patient 10 and/or general patient information based (J).

Additionally, in some embodiments the system 202 can adjust the HLM 110 and/or one or more of the monitoring devices 218A-N based on the practitioner 210's decision in K. In other examples, and as described throughout, the practitioner 210 can, instead of the computing system 202, manually perform the procedure adjustments or updates. Simultaneously and/or at different times, the system 202 can transmit the updated patient(s) information to the hospital database 206 for storage (L).

Real-time conditions can be received from the blood monitoring system 140 and/or the monitoring devices 218A-N throughout D-L. Receiving real-time updates can be advantageous for the computing system 202 to dynamically adjust the algorithms and/or models used to determine patient harm (E). The real-time updates can also be advantageous to dynamically adjust one or more procedure adjustment recommendations that are provided to the practitioner 210 (F). As a result, the practitioner 210 can, if desired, spend less valuable time during the procedure 200 analyzing patient conditions. Moreover, the practitioner 210 does not have to spend valuable time making determinations about whether and what type of procedure adjustment is required to protect the patient 10 from experiencing harm.

Continuous improvement of the algorithms and/or models provides for more accurate predicting of patient harm, individual parameters, and beneficial procedure adjustments. During traditional procedures, it can be challenging for practitioners 210 to perform all the tasks related to the procedure and simultaneously monitor all of the patient's conditions. Usually, the practitioner 210 is alerted once the patient is nearly harmed, and sometimes that can be too late for the practitioner 210 to appropriately address the conditions causing the harm. Once the practitioner 210 is alerted of the potential harm, the practitioner 210 may be under more stress to find a solution. Consequently, the practitioner 210 may make errors in addressing the harm or other aspects of the procedure. The disclosed technology alleviates at least some of these issues by providing proactive rather than reactive predictions, suggestions, and/or solutions to mitigate patient harms.

Figure 2B:
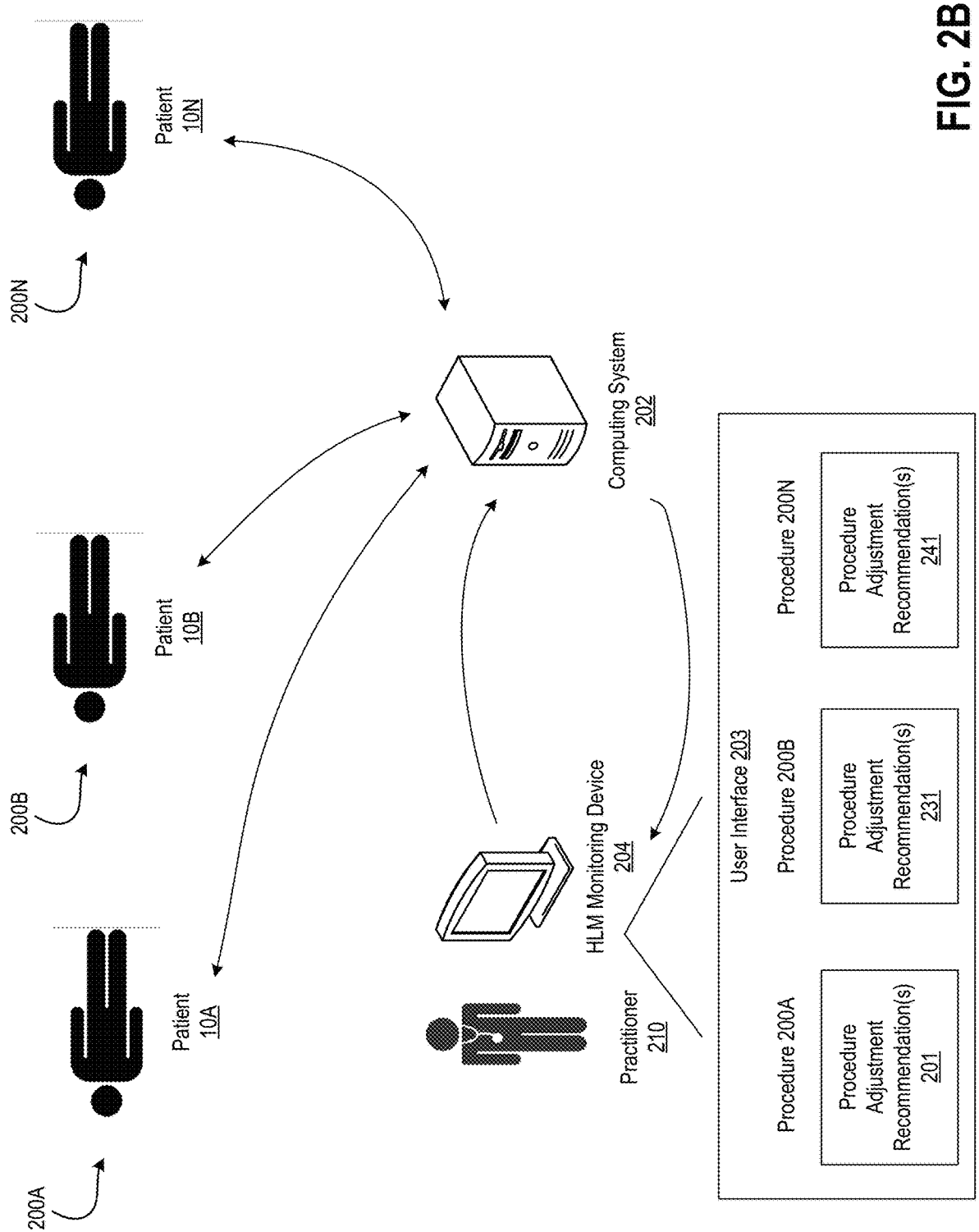

Referring also to FIG. 2B, the example computing system 202 can be used to assist the practitioner 210 in performing and/or overseeing multiple medical procedures 200A, 200B, and 200N on patients 10A, 10B, and 10N, respectively. The medical procedures 200A, 200B, and 200N can be performed simultaneously and/or at different times. In some implementations, the practitioner 210 can monitor the procedures 200A, 200B, and 200N from a remote location (such as a control room) by the HLM monitoring device 204.

As depicted, the computing system 202 can receive and transmit information/data with components/devices in each of the procedures 200A, 200B, and 200N (e.g., refer to FIG. 2A). The system 202 can analyze the patients 10A, 10B, and 10N conditions to determine procedure adjustment recommendations that prevent the patients 10A, 10B, and/or 10N from being harmed during the procedures 200A, 200B, and 200N. The system 202 can transmit such procedure adjustment recommendations to the device 204. The practitioner 210 can select one or more of the procedure adjustment recommendations for one or more of the procedures 200A, 200B, and 200N (e.g., refer to FIG. 2A).

In some examples, when the practitioner 210 selects one or more procedure adjustment recommendations, the recommendations can be transmitted to a device at the procedures 200A, 200B, and/or 200N. The device at the procedures can notify a nurse, junior perfusionist, surgeon or other practitioner at the procedural site (e.g., operating room) to perform such procedure adjustments. This is advantageous because the practitioners performing the actual procedure do not have to analyze the patients' conditions and make determinations about the patients' levels of harm. Instead, the practitioners can focus on performing the procedure and addressing other needful tasks that may arise. In other examples, the selected procedure adjustment recommendations can be automatically performed/implemented by the computing system 202 and/or one or more devices located at the procedures 200A, 200B, and/or 200N (e.g., robotic devices, semi-autonomous robotic devices, etc.). This is advantageous because it provides for the practitioners performing the procedure to focus on the procedure instead of monitoring conditions of the patient and/or conditions of medical devices used during the procedure (e.g., an HLM, urine collection bag monitor, etc.).

In some embodiments, the HLM monitoring device 204 can display an interactive user interface 203. The interface 203 can include information about each of the procedures 200A, 200B, and 200N. The displayed information can include real-time updates/conditions of the patients 10A, 10B, and/or 10N (not depicted) and procedure adjustment recommendation(s) 201, 231, and 241. The interface 203 can also display trend analysis of different conditions per patient using 2D and/or 3D graphs, etc. (e.g., refer to FIGS. 7B-7D).

Since the single practitioner 210 can oversee and monitor multiple procedures at a time while performing or selecting procedure adjustments that prevent patients from experiencing harm and/or optimizes patient outcomes, hospital and medical costs can be reduced. Consequently, patient safety can be improved. Moreover, in some implementations, real-time conditions about the patients 10A, 10B, and 10N can be used by the computing system 202 to determine procedure adjustment recommendations for each of the respective procedures 200A, 200B, and 200N. For example, if patients 10A, 10B, and 10N are undergoing the same medical procedure, the computing system 202 can analyze patient 10A's reaction to one or more procedure adjustments in the procedure 200A to determine what procedure adjustment recommendations to generate for the procedures 200B and 200N. Such dynamic data analysis provides for more robust and accurate real-time procedure adjustment generation.

In traditional medical procedures, practitioners do not have the time or capability to review and analyze data about different patients who simultaneously undergo the same procedures. The disclosed technology, therefore, makes it possible to integrate data in real-time from different sources to generate patient harm predictions and procedure adjustment recommendations. Moreover, this dynamic data analysis can be advantageous to continuously improve the algorithms and/or models that the computing system 202 uses to predict patient harm and determine optimal procedure adjustment recommendations.

Figure 3:
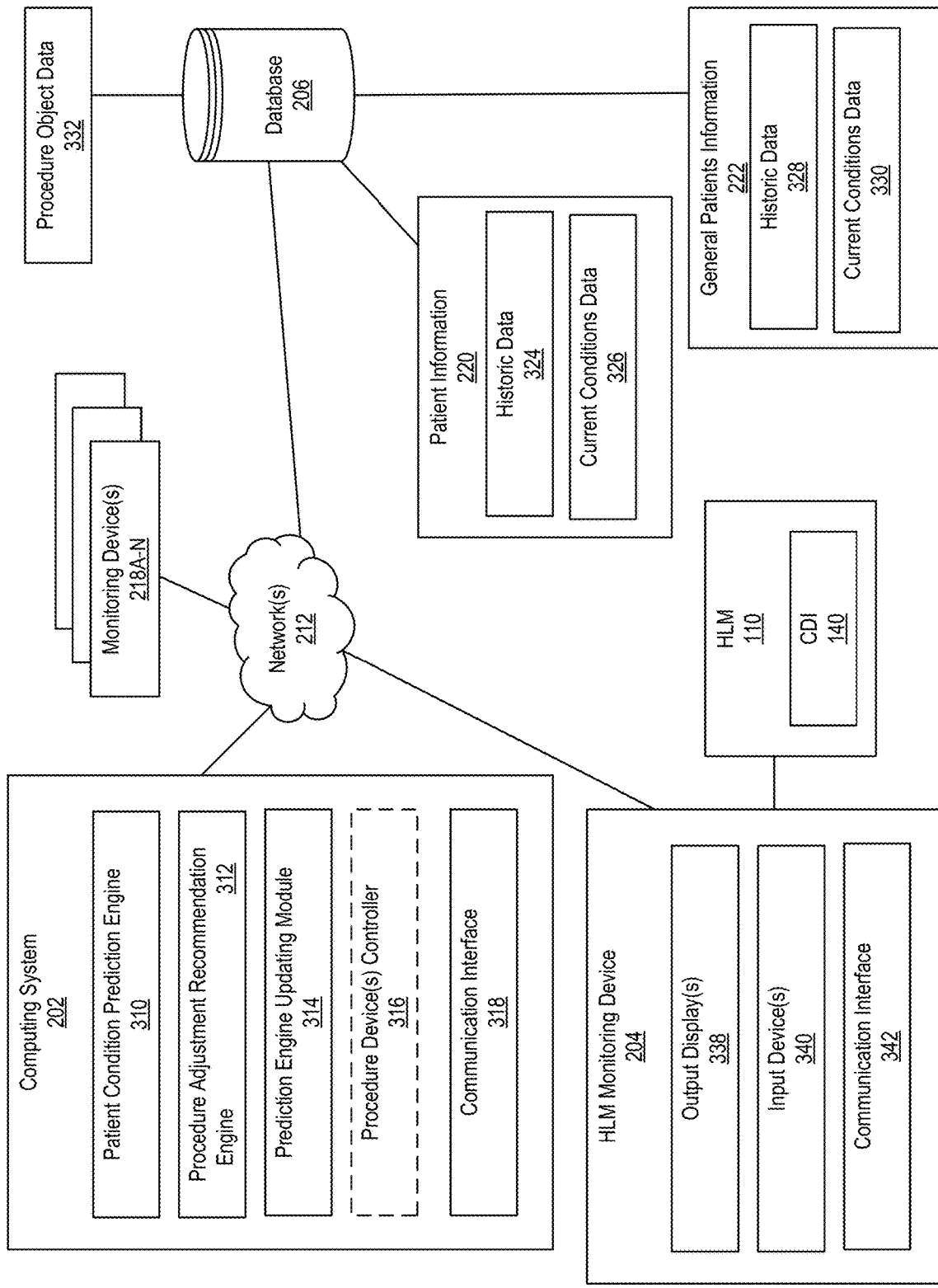
FIG. 3 is a schematic diagram of an example system for performing a semi-autonomous medical procedure as described herein.

FIG. 3 is a schematic diagram of the example computing system described herein. Computing system 202, monitoring device(s) 218A-N, database 206, and HLM monitoring device 204 are in communication (e.g., wired and/or wireless) via network(s) 212. The database 206 can be associated with a particular medical institution, such as a hospital, where one or more of the procedures occur. In other examples, the database 206 can be remote storage (e.g., in a cloud) that collects and stores anonymized patient data across different medical institutions.

In the depicted example, the computing system 202 includes a patient condition prediction engine 310, a procedure adjustment recommendation engine 312, a prediction engine updating module 314, an optional procedure device(s) controller 316, and a communication interface 318.

The patient condition prediction engine 310 can be configured to predict how a patient is going to respond to a medical procedure. The engine 310 can predict one or more safety ranges associated with different parameters that are monitored during the procedure. Understanding how each parameter may fluctuate during the procedure is beneficial to determine an overall condition or health of the patient. Understanding how each parameter fluctuates can also be beneficial to generate adjustments to one or more monitoring devices and other procedure devices. The engine 310 can determine patient condition(s) and parameter safety ranges based at least in part on patient information 220, general patients information 222, and/or procedure object data 332 that are received from the database 206. The engine 310 can predict patient conditions and parameter safety ranges before, during, and/or after the medical procedure. Moreover, the engine 310 can adjust the predicted patient conditions and/or parameter safety ranges in real-time based on sensed conditions of the patient during the procedure.

The patient information 220 can be specific to the patient undergoing the medical procedure. The information 220 can include historic data 324 about the specific patient and/or current conditions data 326 about the patient. The current conditions data 326 can optionally include real-time information that is sensed by one or more of the monitoring device(s) 218A-N during the medical procedure. In some implementations, the data 326 can include data collected about the patient from previous similar procedures. In yet other implementations, the data 326 can include blood panels, ECG, EEG, echo-grams, medications, skin conductivity, and/or any other vital signs that are monitored before, during, and after the medical procedure. Moreover, the historic data 324 can include age, area of residence, clinician notes, diagnoses, diet, gender, medical records, medications, race, sex, supplement and/or vitamin intake, etc. Additional information about the specific patient, such as atmospheric intake, dietary intake, typical stress levels, and water intake can be beneficial to determine how the patient will respond to the medical procedure in comparison to other patients.

The general patients information 222 can include historic data 328 about patients who have undergone similar procedures as the specific patient and/or have similar health conditions/vitals as the specific patient. The information 222 can also include current conditions data 330 of other patients who are undergoing similar and/or the same procedure as the specific patient. The information 222 can include information that may not appear relative to a human observer but is relative to algorithms used by the computing system 202. Information such as area of residence, atmospheric intake, dietary intake, typical stress levels, and/or water intake can, in some cases, prove beneficial for the computing system 202 to more accurately predict different patient conditions and responses during a medical procedure.

The procedure object data 332 can include information about a device and/or object that is being used before, during, and/or after the medical procedure. For example, the procedure object can be any living or nonliving item that is to remain installed in, on, and/or with the specific patient during and/or after the medical procedure. The object can be permanent, semi-permanent, or temporary. Non-limiting examples of the procedure object include the patient's appendix, a biopsy, a heart valve, a kidney stone, a knee replacement, an organ transplant, a pacemaker, and a tonsil. The data 332 can include a composition, condition, lot number, part number, status, profile, transport history, or any other information relevant to perform the procedure with the procedure object. The procedure object data 332 can also include information and/or conditions about devices that are attached to the patient during a medical procedure, including but not limited to electro-cautery knives, HLMs (via cannulae/tubing), intra-venous devices, robotic joint replacement assistance devices, long-term micro-infusion devices, urinary catheters, and ventilators.

Referring back to the computing system 202, the procedure adjustment recommendation engine 312 can communicate with the patient condition prediction engine 310. The engine 312 can determine what procedure adjustments should occur during the medical procedure to prevent the patient from being harmed. The engine 312 can also determine procedure adjustments to prevent one or more of the monitored parameters from exceeding upper and lower limits of the associated safety ranges (e.g., refer to FIGS. 7A-7C).

The engine 312 can generate one or more procedure adjustment recommendations that are communicated to the HLM monitoring device 204. A practitioner at the device 204 can select one or more of the generated procedure adjustment recommendations to perform. As a result, the selected procedure adjustment can be performed manually by the practitioner and/or automatically (e.g., autonomously and/or semi-autonomously) by the computing system 202. The adjustment can also be performed by a device located at the site of the procedure and/or in communication with the HLM monitoring device 204 and/or the computing system 202. In a preferred instance, the procedure adjustment can be performed essentially immediately such that the predicted harm to the patient does not occur. As a result, the patient can remain in a safe condition (e.g., safe range, target range, ideal range) before, during, and after the medical procedure.

The monitoring device 204 can have an output display(s) 338, input device(s) 340, and a communication interface 342. The output display 338 can be configured to output the one or more procedure adjustment recommendations generated and provided by the computing system 202. The display 338 can also output one or more real-time conditions of the patient during the medical procedure. Additionally, the output display 338 can display conditions sensed by the blood monitoring system 140 of the HLM 110.

In some embodiments, the practitioner can monitor and/or control the HLM 110 using the monitoring device 204. The input device 340 can receive the practitioner's selection of one or more of the procedure adjustment recommendations. The input device 340 can also receive commands from the practitioner for a semi-autonomous action to be taken. For example, the practitioner can remotely adjust blood flow levels in the HLM 110 using the input device 340. In some implementations, the input device 340 and the output display 338 can be one device, such as a touchscreen. In other implementations, the input device 340 can be at least one of a keyboard, a mouse, a microphone, or any other conventional input device. Finally, the communication interface 342 can provide for communication between the monitoring device 204 and one or more other components, devices, or systems described herein.

Referring back again to the computing system 202, the prediction engine updating module 314 can be configured to continuously update AI, ML, and/or DL algorithms and models that are used by the computing system 202 to predict conditions of the patient, predict safety ranges, and generate procedure adjustment recommendations. The module 314 can make continuous improvements based at least on what procedure adjustments are selected by the practitioner. Continuous improvements can also be based on how the patient responds to the selected procedure adjustments. Moreover, continuous improvements can be based on how a general population of patients would be expected to respond to the selected procedure adjustments. Continuous improvement can also be based on how a general population of practitioners would be expected to respond to recommended procedure adjustments. Furthermore, continuous improvements can be based on real-time conditions that are sensed during the procedure in relation to the patient, the HLM 110, and/or the object that is being used during the procedure. Continuous improvements can be advantageous to ensure that the computing system 202 makes accurate and reliable patient condition predictions and procedure adjustment recommendations for each medical procedure, regardless of specific patient or procedural information.

The module 314 can be configured to provide the database 206 with updated information regarding the patient, general patients, and the procedure object. For example, the module 314 can generate a model for the specific patient indicating how the patient responded to the procedure and is expected to respond to similar procedures. This model can be stored in the patient information 220 and accessed by the computing system 202 during subsequent similar procedures to more quickly and accurately predict how the patient will respond and to determine what procedure adjustment recommendations to generate. This model can further be updated, modified, and/or refined by the module 314 during each subsequent procedure. Doing so can ensure more accurate predictions for the patient in the future. As another example, the module 314 can generate one or more models based on generalized and anonymous patients who underwent similar and/or same procedures. Such models can be stored in the general patients information 222 and accessed when a specific patient undergoes a procedure that is modeled. The model can be used to more accurately predict how the specific patient will respond to the procedure by comparing the patient's conditions to those that are modeled for general patients.

Still referring to the computing system 202, in some embodiments the procedure device(s) controller 316 can be configured to operate/control one or more devices that are used during and/or to perform the medical procedure. For example, in an autonomous or semi-autonomous medical procedure, the controller 316 can be instructed to perform/implement a procedure adjustment suggestion that is generated by the engine 312. In some embodiments, the controller 316 can perform the procedure adjustment without confirmation and/or input from a practitioner at the monitoring device 204. In other implementations, such as when a single practitioner oversees several procedures from a remote location, the practitioner can provide input to the computing system 202 that instructs the controller 316 to perform a selected procedure adjustment on behalf of the practitioner (e.g., semi-autonomous medical procedure). The practitioner can then remotely monitor the procedure adjustment as it is performed by the controller 316. In yet other implementations, the practitioner can select a procedure adjustment at the monitoring device 204 and then manually perform/implement the procedure adjustment. In such a scenario, the controller 316 may not be actuated.

Finally, the communication interface 318 provides for the computing system 202 to communicate with one or more of the components described herein.

Figure 4:
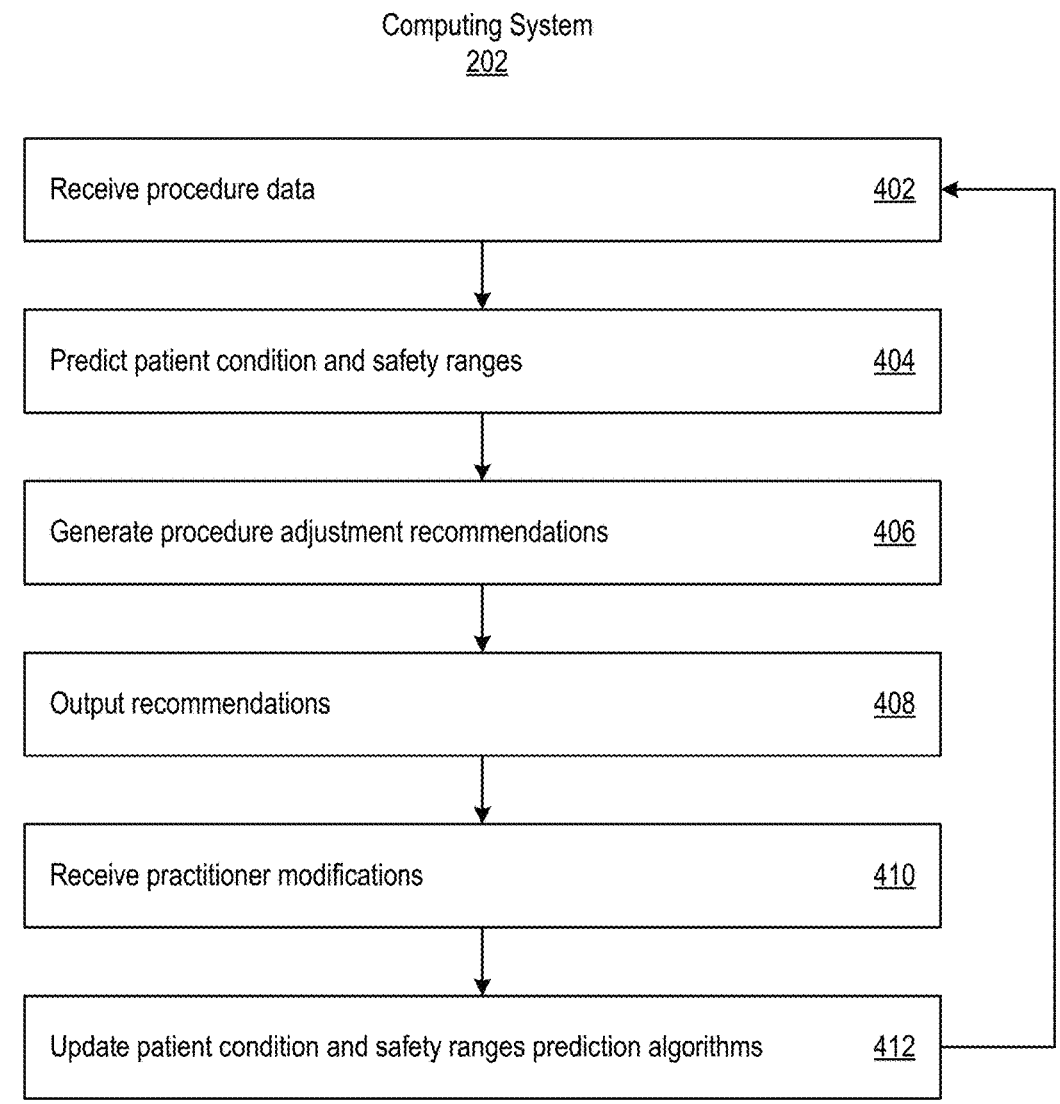
FIG. 4 is a flowchart of a process to perform a semi-autonomous medical procedure.

FIG. 4 is a flowchart of an example method 400 for performing a semi-autonomous medical procedure. The method 400 can be performed by a computing system, as described throughout this disclosure (e.g., computing system 202).

In step 402, procedure data can be received. As described herein, procedure data can include historic and real-time information about a patient undergoing the procedure. The data can be received before, during, and after the procedure. The procedure data can also include historic anonymized data about general patients, procedure objects, and other devices that are used during the procedure.

In step 404, one or more patient conditions and parameter safety ranges can be predicted. One or more of the data received in step 402 can be applied to AI, ML, and/or DL models and/or algorithms to predict how the patient is going to respond to the medical procedure. This information can also be used to determine upper and lower limits of safety ranges for each of the parameters being monitored during the procedure (e.g., refer to FIGS. 7A-7C). Step 404 can be performed before the procedure begins. Predictions made in step 404 can then be continuously updated, if need be, during the procedure.

Procedure adjustment recommendations can be generated in step 406. As described below, the procedure adjustment recommendations can be generated based on determining a range in which the patient will experience normal or safe conditions during the procedure. The computing system described herein can determine that the patient is predicted to deviate from an overall safe range (e.g., a target range or ideal range) at a certain time. The computing system can also determine that one or more parameters are expected to deviate from safety ranges (e.g., target ranges) associated with the one or more parameters. As a result, the computing system can generate an appropriate adjustment suggestion that can be applied to the procedure at a time before the time that the patient and/or any of the parameters are predicted to deviate from their associated safety ranges. When that adjustment is implemented during the procedure, the patient conditions can be maintained within the safety range, thereby avoiding the predicted harm. Further, adjustments can keep patient conditions in an ideal range (target range), thereby maximizing patient outcomes.

In step 408, the procedure adjustment recommendations can be outputted to a display of a computing device. Step 408 can be performed at a later time than steps 402-406. For example, steps 402-406 can be performed before the medical procedure begins. Step 408 can be performed at a time during the medical procedure in which the computing system determines procedure adjustment should occur to maintain the patient or any of the parameters within their associated safety ranges. A practitioner at the computing device can select one or more of the recommendations and the selected recommendation(s) can be received by the computing system in step 410.

A patient condition prediction algorithm can be updated in step 412. Additionally and/or alternatively, one or more other AI, ML, or DL models can be updated to more accurately predict patient conditions, safety ranges, and procedure adjustment recommendations for subsequent procedures and patients. Steps 402-412 can be continuously repeated for a duration of a medical procedure, as well as before and/or after the medical procedure.

Figure 5A:
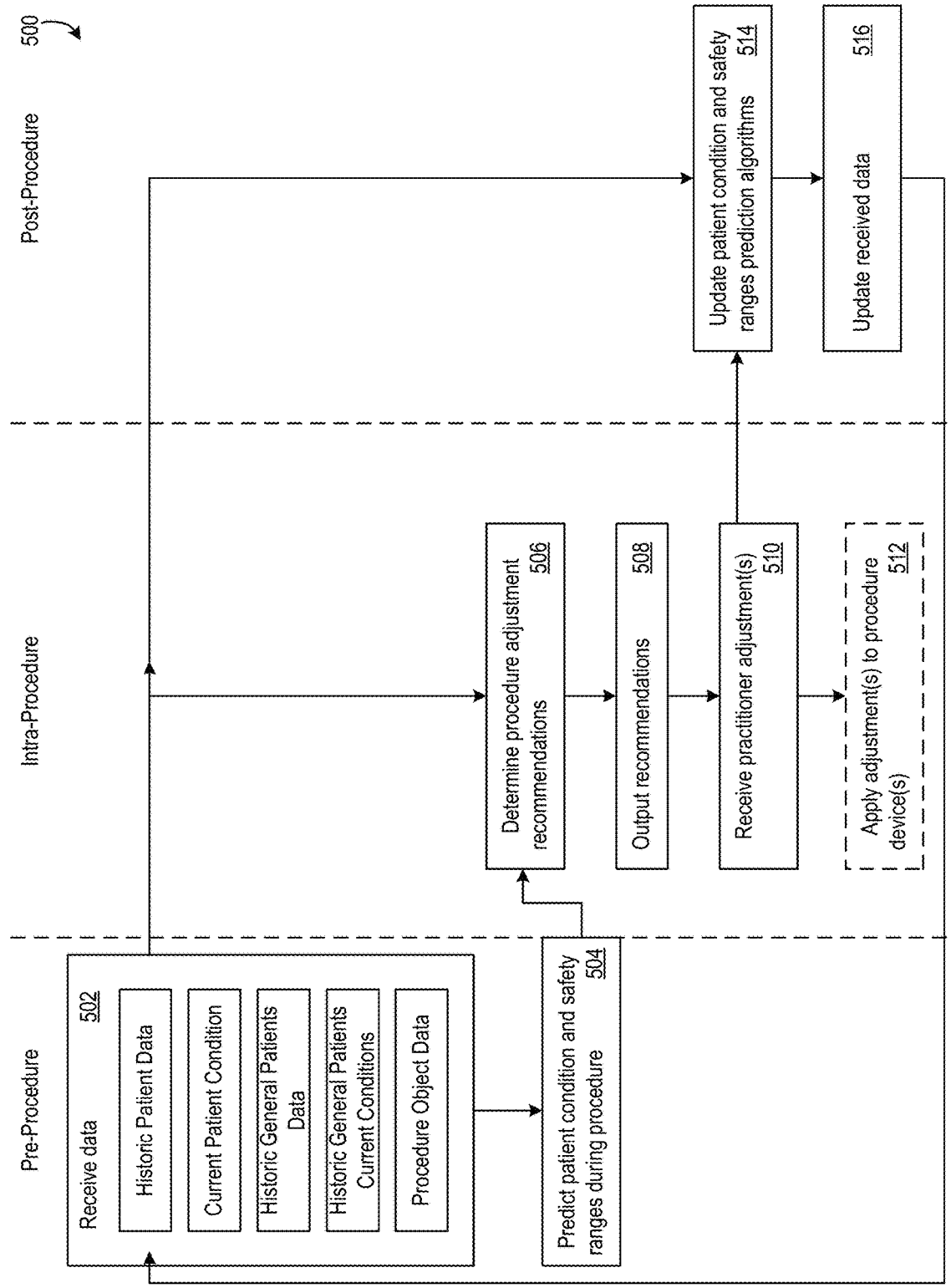
FIGS. 5A-5B are flowcharts of example processes to predict patient conditions before, during, and after a semi-autonomous medical procedure.
Figure 5B:
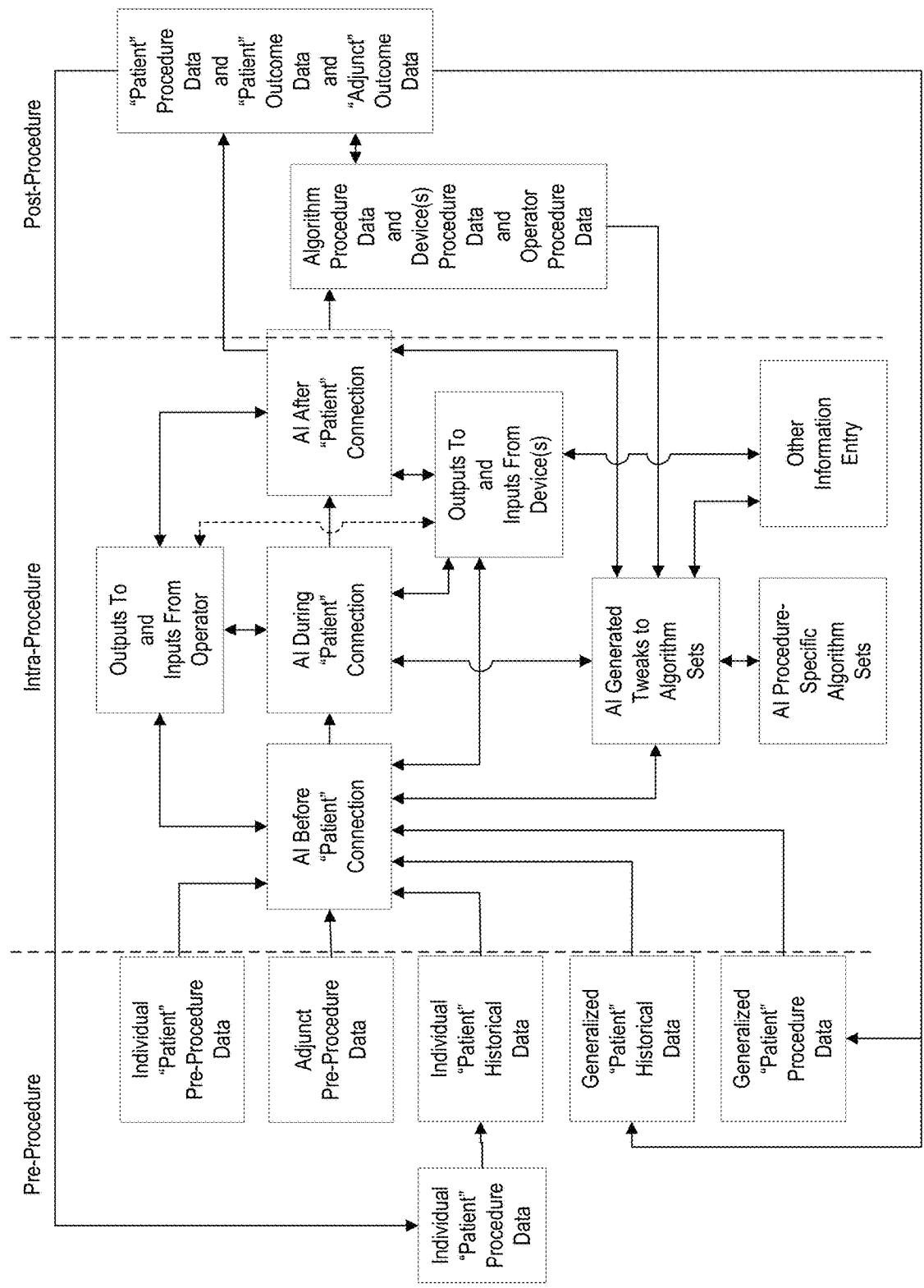

FIGS. 5A-5B are flowcharts of a process 500 to predict patient conditions before, during, and after a semi-autonomous medical procedure. The process 500 can be performed by a computing system as described herein (e.g., computing system 202). One or more steps of the process 500 can be performed during different times of the medical procedure. For example, referring to FIG. 5A, steps 502-504 can be performed pre-procedure, or before the medical procedure begins. Steps 506-512 can be performed intra-procedure, or while the medical procedure is underway. Steps 514-516 can be performed post-procedure, or after the medical procedure is completed.

In some examples, pre-procedure steps can be performed immediately before the medical procedure begins. In other examples, pre-procedure steps can be performed a certain amount of time before the medical procedure begins. Intra-procedure steps can be dynamically adjusted based on conditions sensed and received in real-time. Moreover, in some implementations, patient conditions can be predicted intra-procedure as well as pre-procedure. Post-procedure steps can be performed immediately after the medical procedure is completed. In some examples, post-procedure steps can be performed a certain time after the medical procedure. As a result, conditions of a patient's recovery can be analyzed and used to enhance the algorithms, ML, and/or AI techniques used to predict patient conditions.

Still referring to the process 500 in FIG. 5A, data can be received in step 502 pre-procedure. As described herein, the data can include historic patient data, current patient condition(s), historic general patients data, historic general patients current condition(s), and procedure object data. Data can be continuously received from one or more sources (e.g., monitoring devices 218A-N, blood monitoring system 140, hospital database 206) during the pre-, intra-, and post-procedure phases. For example, during the intra-procedure phase, historic data about the patient can be received to diagnose and/or analyze a unique condition that the patient is experiencing during the procedure. Historic data about general patients can also be beneficial during this phase to determine whether the patient is currently experiencing any condition that is atypical for the procedure. As another example, during the post-procedure phase, current patient conditions and historic general patients current conditions can be received to determine whether the patient is recovering from the procedure in a way that is atypical from the general population of patients who underwent the same procedure.

Once relevant data is received in step 502, a patient condition during the procedure can be predicted in step 504. Additionally and/or optionally, one or more parameter safety ranges can be determined in step 504 (e.g., refer to FIGS. 7A-7C). Step 504 can be performed pre-procedure. Step 504 can also be performed intra-procedure. Whether or not step 504 is performed pre- or intra-procedure, the prediction of patient conditions during the procedure can be dynamically adjusted to accommodate for real-time changes in the patient's condition. The algorithms, models, ML techniques, and/or AI used by the computing system to make predictions in step 504 are continuously trained on historic data as well as real-time data. Consequently, patient condition predictions can be more accurately generated pre-procedure. Patient condition predictions may not need to be modified and/or adjusted during the intra-procedure phase. This can reduce a time needed to generate potential procedure adjustment recommendations and apply such modifications before the patient is harmed. As a result, patient safety can be improved.

Once the patient conditions and/or safety ranges are predicted in step 504, procedure adjustment recommendations can be determined in step 506. This step can occur during the intra-procedure phase. As another example, this step can occur pre-procedure. The procedure adjustment recommendations can be determined based at least in part on real-time conditions received from one or more components used during the medical procedure. For example, blood oxygen content can be continuously monitored by a blood gas monitor (e.g., CDI® monitor) as the blood flows between an HLM and the patient's body. Based on real-time changes in the blood oxygen content, the computing system can generate one or more procedure adjustments to adjust the HLM. Step 506 can be performed pre-procedure based on applying one or more algorithms, machine learning, and/or artificial intelligence techniques described herein. Such techniques can be used to analyze historic patient and general patients conditions during similar procedures in which one or more procedure adjustment recommendations were generated and/or implemented.

Moreover, the techniques described herein can be used to generate fewer procedure adjustment recommendations in step 506. For example, a trained ML model can predict, based on all the data received in step 502, that only one procedure adjustment will prevent the patient from being harmed. In other words, the more trained the techniques described herein are, the more accurately they can determine fewer, more effective procedure adjustment recommendations. Providing fewer procedure adjustment recommendations to a practitioner can also prevent the practitioner from being overloaded with information during the medical procedure. The practitioner will be less overwhelmed to make a decision about modifying the procedure and can focus on performing the procedure, ensuring patient safety, and optimizing patient outcomes.

During an autonomous procedure, where the trained ML model or other techniques described herein generate one procedure adjustment, that procedure adjustment can be quickly and automatically implemented. This is because the computing system would not have to compare multiple procedure adjustment recommendations to identify and select the most optimal one. This improves efficiency in the medical procedure. This also reduces risk of the patient experiencing harm during the procedure.

Once the procedure adjustment recommendations are determined in step 506, the recommendations can be outputted in step 508 during the procedure. As described throughout, the recommendations can be outputted to a display of a monitoring device of the practitioner (e.g., HLM monitoring device 204). The practitioner can select one or more of the recommendations at the monitoring device.

The practitioner's selection is received by the computing system in step 510. Based on the practitioner selection, the computing system can apply the modification to one or more of the related procedure devices in step 512 (e.g., the computing system can send a signal to the HLM to adjust a blood flow rate). In other examples, the practitioner can select the modification and manually perform that modification.

The patient condition and safety ranges prediction algorithms, or other machine learning and/or artificial intelligence techniques and models described herein, can be updated in step 514. The updates can be based at least in part on what procedure adjustment (s) the practitioner selected. The updates can also be based on real-time conditions of the (1) patient, (2) procedure devices, and/or (3) procedure object during and/or after the medical procedure. Step 514 can be performed post-procedure. Step 514 can also be performed intra-procedure. Performing step 514 during the procedure is beneficial to more accurately and dynamically determine procedure adjustments.

In step 516, data received in step 502 can be updated post-procedure. The data can be continuously updated in real-time (e.g., during the medical procedure). Updating the data in real-time can be advantageous so that the updated data can be used in predicting patient conditions and determining procedure adjustment recommendations during the medical procedure. Once the data is updated, the data can be stored (e.g., in the database 206).

The steps 502-516 can be continuously repeated and/or repeated a certain number of times. Repeating the process 500 is advantageous to continuously improve and enhance the modeling and predictive techniques described herein. As a result, more accurate and reliable patient condition predictions and procedure modification recommendations can be generated.

FIG. 5B is another example of the process 500 described in reference to FIG. 5A. As depicted, a medical procedure is broken up into three phases: pre-procedure, intra-procedure, and post-procedure. During the pre-procedure phase, individual patient procedure data, which was collected during a medical procedure, is stored with individual patient historical data. Pre-procedure, individual patient pre-procedure data (e.g., heartrate before the procedure begins), adjunct pre-procedure data (e.g., information about a living or non-living object that is used and/or inserted into and/or removed from the patient before, during, or after the procedure), individual patient historical data, generalized patient historical data, and generalized patient procedure data can be collected. This data can be used by the algorithms, ML, and/or AI techniques described herein. The patient pre-procedure data can include pre-procedure response testing data. For example, an EKG-connected patient can be exposed to temporary trial-doses of anesthetic and/or drugs (e.g., non-routine stressors) to characterize the patient's behavior, response, and/or safety. Data collected about the patient's response to the trial-doses can be used to refine algorithms or other techniques used to more accurately predict patient conditions. This data can also be used to more accurately determine patient safety ranges, limits, and initial settings for the medical procedure.

The data described above can be used intra-procedure to determine a patient condition before the procedure (e.g., refer to "AI Before "Patient" Connection" box in FIG. 5B), a patient condition during the procedure (e.g., refer to "AI During "Patient" Connection" box in FIG. 5B), and a patient condition after the procedure (e.g., refer to "AI After "Patient" Connection" box in FIG. 5B). One or more of the algorithms, ML models, and/or AI techniques described herein can be used to determine these conditions. Accordingly, procedure adjustment recommendations can be generated intra-procedure. One or more of the predicted conditions can be outputted to a device of an operator (e.g., practitioner). Inputs (e.g., practitioner selection of a procedure modification recommendation) can also be received from the device of the operator. Information received from the device of the operator can be used to refine and/or adjust predictions of the patient before, during, and after the procedure.

Information can also be received from one or more other devices used during the procedure, such as patient monitoring devices and procedure devices. This information can be used by one or more of the techniques described herein to refine and/or adjust predictions of the patient conditions before, during, and after the procedure. The patient predictions as well as the procedure modification (e.g., adjustment) recommendations can be outputted to one or more of the devices (e.g., an HLM's settings can be automatically adjusted).

The algorithms and other techniques used and described herein can be continuously modified (e.g., refer to "AI Generated Tweaks to Algorithm Sets" box in FIG. 5B). The techniques described herein can be initially set by a human. Using AI and/or DL, the techniques can be continuously and iteratively improved. Moreover, adjustments to the techniques can include continuous improvements of procedure-specific algorithm sets (e.g., refer to "AI Procedure-Specific Algorithm Sets" box in FIG. 5B). In other words, an algorithm that is used to predict how a specific patient is going to respond to a specific procedure can learn from and adjust accordingly based on improvements made to other algorithms. The other algorithms, for example, can predict how a general patient will respond to a similar or more generalized procedure. As a result, algorithms can learn from each other to further refine their techniques, even though the algorithms are tailored to generating predictions about different devices, procedures, and/or patients. Such continuous refinement can improve the ability of any of the algorithms used to more accurately predict patient conditions and procedure adjustment recommendations. The algorithms described herein can also be improved using information received from different sources, including a hospital laboratory information management system and remote databases or data warehouses (e.g., refer to "Other Information Entry" box in FIG. 5B).

Monitoring, treatment, and even procedure-related equipment can follow the patient in post-procedure settings. Therefore, the disclosed technology can continue to evaluable information/data collected pre-, intra-, and post-procedure. As a result, patient recovery conditions can be predicted. Post-procedure, patient procedure data, patient outcome data, and adjunct object outcome data can be updated based on the predictions made during the procedure. The updated data can be fed back into the pre-procedure phases of collecting generalized patient historical and procedure data as well as the individual patient historical data. The patient outcome data can be collected over time. It can include a subset of or consist of complete patient post procedure history. This information can be beneficial to one or more of the techniques described herein when predicting patient conditions and/or procedure adjustment recommendations. The adjunct object outcome data can include any information regarding an adjunct item (e.g., object) that alters (or confirms no alteration) of its "Adjunct Pre-Procedure Data" and/or that creates information newly generated during the procedure about the adjunct item. This information can be interrelated with the patient pre-procedure data. This information can also be interrelated with the patient outcome data.

The patient procedure data, patient outcome data, and adjunct object outcome data can also be fed into an algorithm or model along with procedure data, device procedure data, and operator procedure data. The device procedure data can include a record of all inputs, outputs, and any other information collected from each of the devices used during the procedure. The operator procedure data can include a record of all actions taken by the operator (e.g., practitioner) during the procedure. The algorithm can include a record of all actions, observations, and/or real-time conditions documenting what happened during the procedure. The algorithm can be used to enhance and adjust/tweak one or more of the algorithms or other techniques used during the procedure (e.g., the AI generated tweaks to algorithm sets and the AI procedure-specific algorithm sets). As a result of continuously improving the techniques described herein, more accurate predictions can be made before, during, and after a medical procedure to prevent patient harm, improve patient safety, and reduce costs of medical procedures.

Figure 6A:
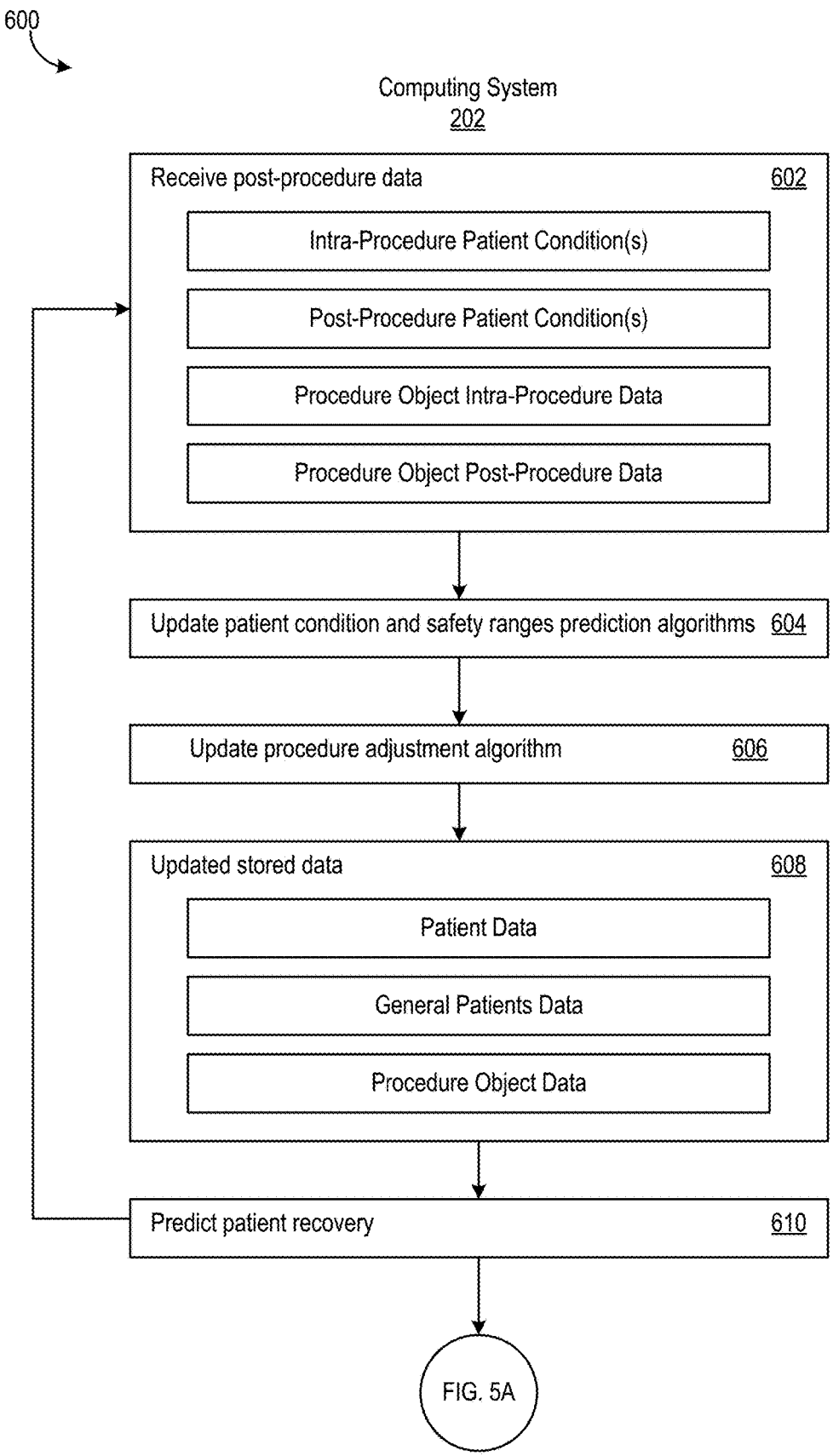

FIGS. 6A-6C are flowcharts of a process 600 to improve predicting patient conditions after a semi-autonomous medical procedure is completed. The process 600 can be performed by a computing system, as described throughout this disclosure.

Referring to FIG. 6A, post-procedure data can be received in step 602. As described in reference to FIGS. 5A-5B, the post-procedure data can be intra-procedure patient condition(s), post-procedure patient condition(s), procedure object intra-procedure data, and/or procedure object post-procedure data. Using the data received in step 602, a patient condition prediction algorithm as described herein can be updated in step 604. A procedure adjustment algorithm as described herein can also be updated in step 606. Next, stored data can be updated in step 608. Patient data, general patients data, and procedure object data can be updated based at least in part on the post-procedure data. Once information and/or algorithms are updated, patient recovery can be predicted in step 610. The predicted patient recovery can also be based on real-time conditions or other information received from devices that are connected to the patient during and after the procedure. The steps 602-610 can repeat continuously and/or for a predetermined time. Patient recovery predictions can then be adjusted based on real-time conditions post-procedure. After the patient recovery is predicted in step 610, the process 500 described in reference to FIG. 5A can be performed.

FIGS. 6B-6C are additional examples of the process 600 described in reference to FIG. 6A. FIG. 6B depicts how algorithms described herein are used to continuously improve and/or update patient data. For example, as described in reference to FIG. 5B, an algorithm is applied to analyze and determine trends about procedure data, device procedure data, operator procedure data, patient procedure data, patient outcome data, and adjunct object outcome data. Insight gleaned from such analysis can be stored as the adjunct post-procedure data, the individual patient procedure data, the generalized patient historical data, and the generalized patient procedure data. Information from one or more other post-procedure data sources (e.g., manually entered by the operator) can be incorporated into the adjunct post-procedure data and the individual patient procedure data. As depicted in FIG. 6B, updating and/or refining the data and algorithms used to predict patient conditions and procedure modifications is a continuous process. Doing so ensures that the algorithms used to make these predictions are accurate and reliable.

FIG. 6C depicts how algorithms described herein are used to continuously improve/update the algorithms used to make predictions throughout a medical procedure. For example, as described in reference to FIG. 5B, an algorithm that predicts patient conditions during the procedure can be applied to one or more general algorithm sets to enhance and refine those algorithm sets. One or more procedure-specific algorithm sets can be enhanced and/or refined based on improvements made to the general algorithm sets. As a result, the algorithms and techniques described throughout are continuously improved. Continuous improvement is beneficial to provide for more accurate analysis of patient conditions and procedure adjustment predictions.

In reference to both FIGS. 6B-6C, DL can be used independently and/or with AI or other techniques described herein. DL can augment existing algorithms/algorithm sets, and/or databases that are implemented in the disclosed technology. Pattern recognition is a primary goal for DL, which is seeking relationships between factors not readily observable to humans. As an illustrative example, it may be discovered that individuals who consumed chlorinated water for more than 12 consecutive years, and who are predisposed to episodes of gout, are 175% more susceptible to acute kidney injury (AKI). This injury can occur, for example, during cardiopulmonary bypass (CPB) when oxygen delivery (DO2) falls below 272 $mL \cdot min^{-1} \cdot m^{-2}$ for more than 3 minutes. It may also be discovered, for example, that these individuals are 535% more likely of being injured when oxygen delivery either falls below that threshold for more than 5½ minutes or below 250 $mL \cdot min^{-1} \cdot m^{-2}$ for more than 2½ minutes. DL can be implemented in the disclosed technology to analyze data (e.g., historic patient data, current patient data, general patients historic data, general patients current data, research or information from the Internet or other sources, etc.) over extended periods to make these discoveries. Such discoveries can be applied to the techniques described herein to more accurately determine and predict patient conditions, safety ranges, and procedure adjustment recommendations.

Figure 7A:
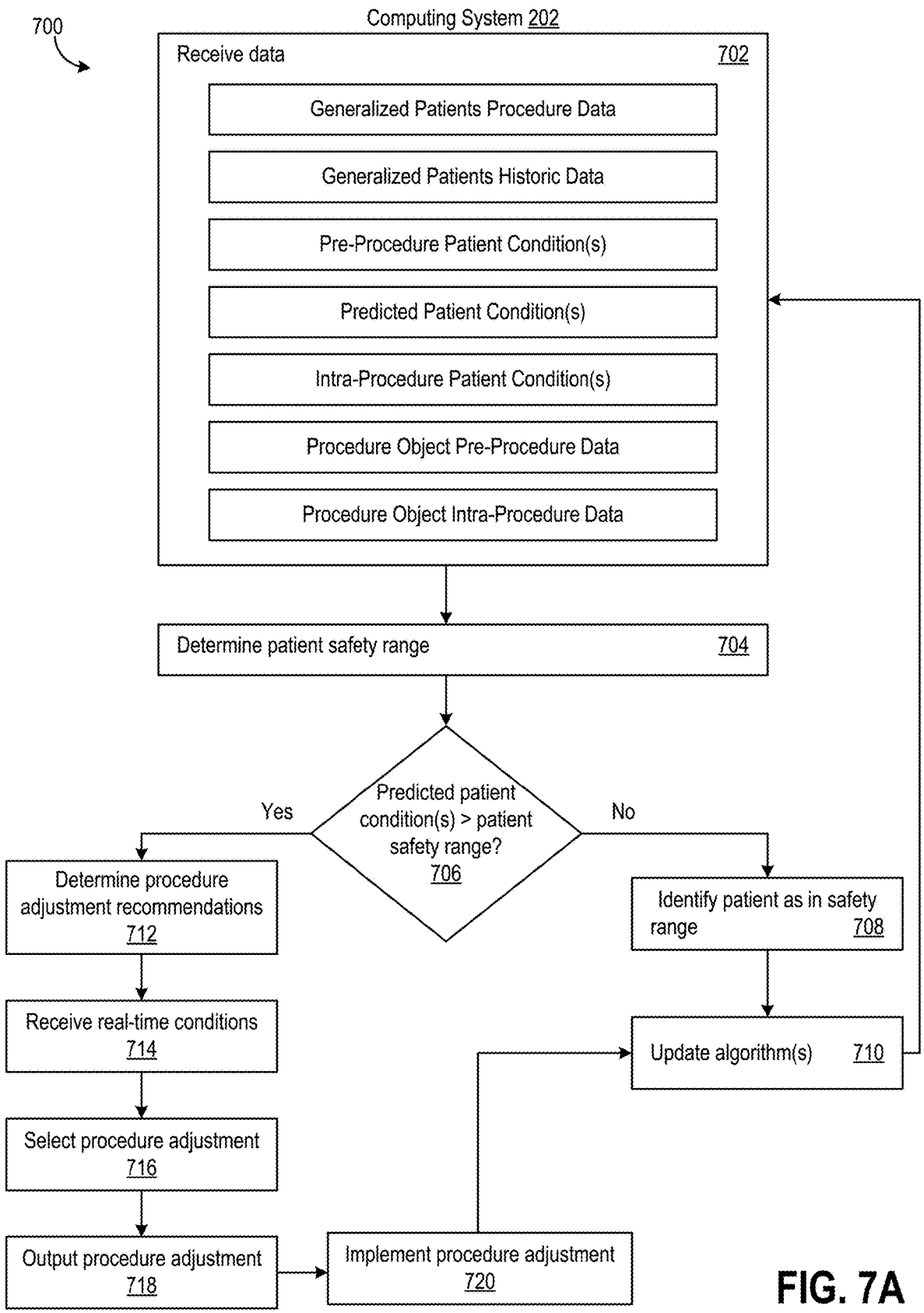
FIG. 7A is a flowchart of an example process for generating procedure modification recommendations.

FIG. 7A is a flowchart of an example process 700 for generating procedure modification recommendations. The process 700 can be performed by a computing system, as described herein.

First, in step 702, data can be received from one or more sources. The data can include generalized patients procedure data, generalized patients historic data, pre-procedure patient condition(s), predicted patient condition(s), intra-procedure patient condition(s), procedure object pre-procedure data, and procedure object intra-procedure data.

Based on the received information, the computing system can determine a patient safety range in step 704. The patient safety range is typically a range for a duration of the procedure in which one or more parameters associated with the patient's health conditions should be maintained. Deviating from that range can result in the patient being harmed. Ideally, the patient should be kept in the safety range. Within the safety range, potential harms can be predicted, addressed, and avoided. As a result, the patient can remain within the safety range during the procedure.

In conventional procedures, often a practitioner does not become notified that the patient is no longer in the safety range until the patient is experiencing some level of harm. At this point, it might be too late and/or risky to make adjustments to the procedure in some cases. The techniques described herein, however, alleviate this problem by helping to ensure that the patient remains within the patient safety range for the duration of the procedure.

Still referring to step 704, the computing system can compare the patient's pre-procedure conditions to generalized patients procedure data. In doing so, the system can determine whether the patient is going into the procedure with different conditions than previous patients. If the patient is experiencing the same or similar conditions, the computing system can determine the patient's safety range based off prior determined patient safety ranges. If, on the other hand, the patient is experiencing different conditions than previous patients, the computing system can analyze other data that was received in step 702 to determine an optimal safety range for this particular patient. The determined patient safety range can also adapt and/or change over time based on the predicted patient conditions, patient conditions recorded during the procedure, conditions of the procedure object before the procedure, conditions of the procedure object during the procedure, and the like.

Dynamic adjustment of the patient safety range during the procedure is advantageous to ensure the patient does not experience harm. Dynamic adjustments are also advantageous to ensure that a practitioner adequately and quickly addresses patient safety before the patient is potentially harmed. Moreover, receiving data from multiple sources in real-time provides for more accurate predicting of patient harm and patient safety scenarios. This is because a practitioner, especially during a procedure, may not have the capacity, ability, or time to review and analyze such an abundance of information, and to then make an accurate determination that will dictate whether the patient will be harmed during the procedure.

Once the patient safety range is determined, the computing system can determine whether the predicted patient conditions exceed the patient safety range in step 706. In some examples, the computing system can receive real-time information from one or more monitoring devices that indicate a condition of the patient intra-procedure and/or a condition of the procedure object intra-procedure. This information can be used in addition to the predicted patient conditions to determine a real-time condition of the patient. Consequently, the system described herein can continuously update information pertaining to the patient's conditions to identify whether the patient remains within the safety range. For example, pre-procedure, the process 700 can be performed by the computing system to determine/predict the patient's safety range. During the procedure (e.g., intra-procedure), the safety range can be dynamically updated or modified based on sensed real-time conditions.

Referring back to step 706, if the predicted patient condition(s) exceeds the patient safety range, then the computing system can determine procedure modification recommendations (e.g., adjustments) in step 712. In other words, the system determines that the patient will not be in the safe zone at some point during the procedure and action needs to be taken to prevent the patient from leaving the safe zone. Procedure adjustment recommendations can be made based on analyzing real-time conditions of the patient and comparing the real-time conditions to the pre-procedure conditions. By doing so, the computing system can determine how much the patient conditions changed over a period of time and how long the patient has before the patient may leave the safe zone. Based on such determinations, the computing system can identify how pertinent or aggressive a particular procedure adjustment should be.

Once the procedure adjustments are determined, the computing system can receive real-time conditions of the patient and/or the procedure object in step 714. Using this information, the computing system can select one of the procedure adjustments in step 716. Selection of a preferred procedure modification can be adjusted in real-time based on conditions of the patient in comparison to predictions of how the patient will be. For example, if the real-time conditions indicate that the patient is worse off than the projected/predicted patient conditions, then the computing system can select a more aggressive procedure modification (e.g., adjustment). If, on the other hand, the real-time conditions are in line with the predicted patient conditions, then a more moderate, less extreme procedure modification can be selected. Selecting an optimal procedure modification can also depend on a projected amount of time that it would take for the patient's conditions to exceed the patient safety range. If the patient would eventually deviate from the safety range over a long period of time, then a more gradual procedure modification can be selected. As a result, the patient can still remain in the patient safety range but the patient's body may not be shocked by whatever procedure modification is selected. If, on the other hand, the patient is on the brink of deviating from the safety range, then a more aggressive procedure modification is adopted.

In some implementations, the computing system can select one or more of the procedure adjustment recommendations or not make any selection in step 716. This can be advantageous in semi-autonomous medical procedures in which the practitioner is not only overseeing the procedure but also performing the procedure. As a result, the practitioner can have more ability to control the procedure and make decisions during the procedure. This can also be advantageous in situations where the patient is in the safety range and expected to stay in the safety range without much procedure adjustment. In other words, where the patient's conditions do not fluctuate and/or they only slightly fluctuate, the need for a procedure adjustment is much lower. Thus, more procedure adjustment can be presented to the practitioner and the practitioner can use their discretion to choose whether to adopt any of the procedure adjustments, modify them, or reject them.

Next, in step 718, the selected procedure adjustment(s) can be outputted. As described throughout this disclosure, the selected procedure adjustment(s) can be outputted to a device used by the practitioner, such as an HLM monitoring device. Where multiple procedure adjustments are outputted to the practitioner's device, the procedure adjustments can be ranked in order of preference. For example, the computing system can suggest which of the procedure adjustments would be the best to implement during the procedure. This is advantageous because it saves the practitioner from having to divide their attention and make such decisions while performing the medical procedure. As another example, where the patient is expected to deviate from the patient safety range rather quickly (e.g., the patient's conditions are worsening and without immediate procedure adjustment, the patient will be harmed), the selected procedure adjustment can be outputted with an indication to the practitioner that procedure adjustment is required and must be done immediately. As a result, the practitioner can immediately implement the procedure adjustment without having to spend time making a decision of whether to implement a procedure adjustment and assessing the current condition of the patient. The practitioner can instead focus on other aspects relating to completing the procedure.

Likewise, in step 720, the selected procedure adjustment can be implemented. In some medical procedures, the modification can be implemented by the practitioner. For example, the practitioner can select the modification from the output and then manually perform the modification. In other examples, when the practitioner selects the modification, instructions for completing the modification can be transmitted to a device that performs the modification. By way of example, instructions for adjusting blood flow of an HLM can be sent to the HLM, and/or other controllable devices, such that the HLM, and/or other devices, automatically makes the adjustment. In yet other examples where a practitioner oversees multiple procedures at once, upon selection of the procedure adjustment, instructions to implement the procedure adjustment (e.g., modification) can be transmitted to a device of one or more practitioners performing the procedure such that they can manually and/or semi-autonomously perform the procedure adjustment.

In some implementations, the procedure adjustment can be automatically implemented by the computing system and/or one or more devices in step 720 (e.g., during an autonomous medical procedure). Where procedure adjustment is critical (e.g., the patient is quickly going to deviate from the safety range) and there is not enough time to receive confirmation from the practitioner before implementing the procedure adjustment, then the procedure adjustment can be automatically implemented in step 720.

Once the procedure adjustment is implemented, one or more algorithms used in the process 700 described herein can be updated, as described in further detail below.

Referring back to step 706, if it is determined that the predicted patient conditions does not deviate from the patient safety range, then the computing system can identify that the patient is in the safety range and no procedure adjustment is needed at the time (step 708). The one or more algorithms used in the process 700 can then be updated in step 710. The algorithms can be updated such that even more accurate predictions about the patient's conditions and the patient's safety range can be generated before and during the medical procedure. If predictions before the procedure become more accurate, then changes to such predictions are less likely during the procedure. This would improve efficiency in addressing potential harms to the patient. If the patient conditions and safety range can be identified more accurately, then procedure adjustment recommendations can also be determined and selected more accurately before but also during the procedure. Continuously improving the algorithms and processes described herein is advantageous to ensure that any potential conditions and/or harms can be predicted and addressed before becoming an issue for the patient's wellbeing and safety. As mentioned, all these predictions can be made before a procedure, thereby improving efficiency and accuracy in decision-making during the procedure.

After the algorithms are updated in step 710, steps 702-720 can be repeated. These steps can be repeated a predetermined number of times before or during the procedure. These steps can also be repeated for a duration of the procedure. As described throughout, repeating the process 700 is advantageous to ensure more accurate predictions and dynamic adjustment of predictions, safety ranges, and/or procedure modifications that account for any changes to the patient conditions in real-time.

Figure 7B:
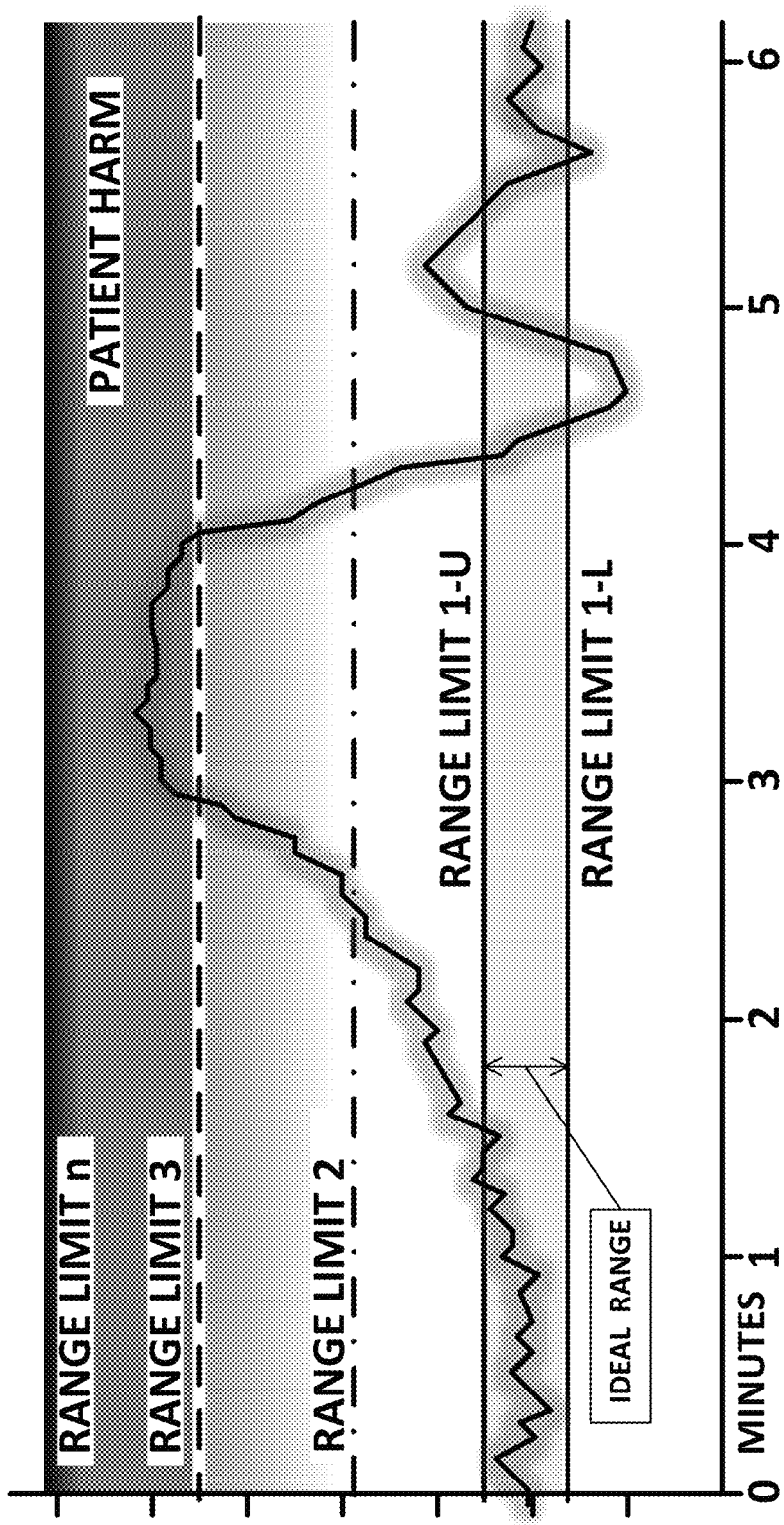
FIG. 7B is an exemplary graph of patient conditions during a traditional, manual medical procedure.

FIG. 7B is an exemplary graph of patient conditions during a traditional, manual medical procedure. Traditionally, a practitioner often does not observe patient conditions trending away from an ideal range (or target range) for some given parameter. Range limit 2 may be set to trigger an alarm/alert, often times being a first indication to the practitioner of a situation requiring procedure adjustment. However, traditionally there is no notice by a device to the practitioner of changes in the patient conditions trend. Any practitioner will need time to analyze why an alert came, consider how to respond, implement a response, and then recognize that the response stopped further progression but did not reverse the situation (e.g., while still in a zone of ongoing patient harm). In some traditional settings, the practitioner may overcorrect then reverse the overcorrection, eventually returning this one given parameter into an apparent steady state in the ideal range. Moreover, other parameters can escape their ideal range while the practitioner is fixated on correcting the given parameter. Therefore, during traditional, manual medical procedures, it can be more challenging for the practitioner to assess and address one or more parameters before such parameters exceed an ideal range, pass the range limit 2, and enter range limit 3, in which the patient experiences harm.

Figure 7C:
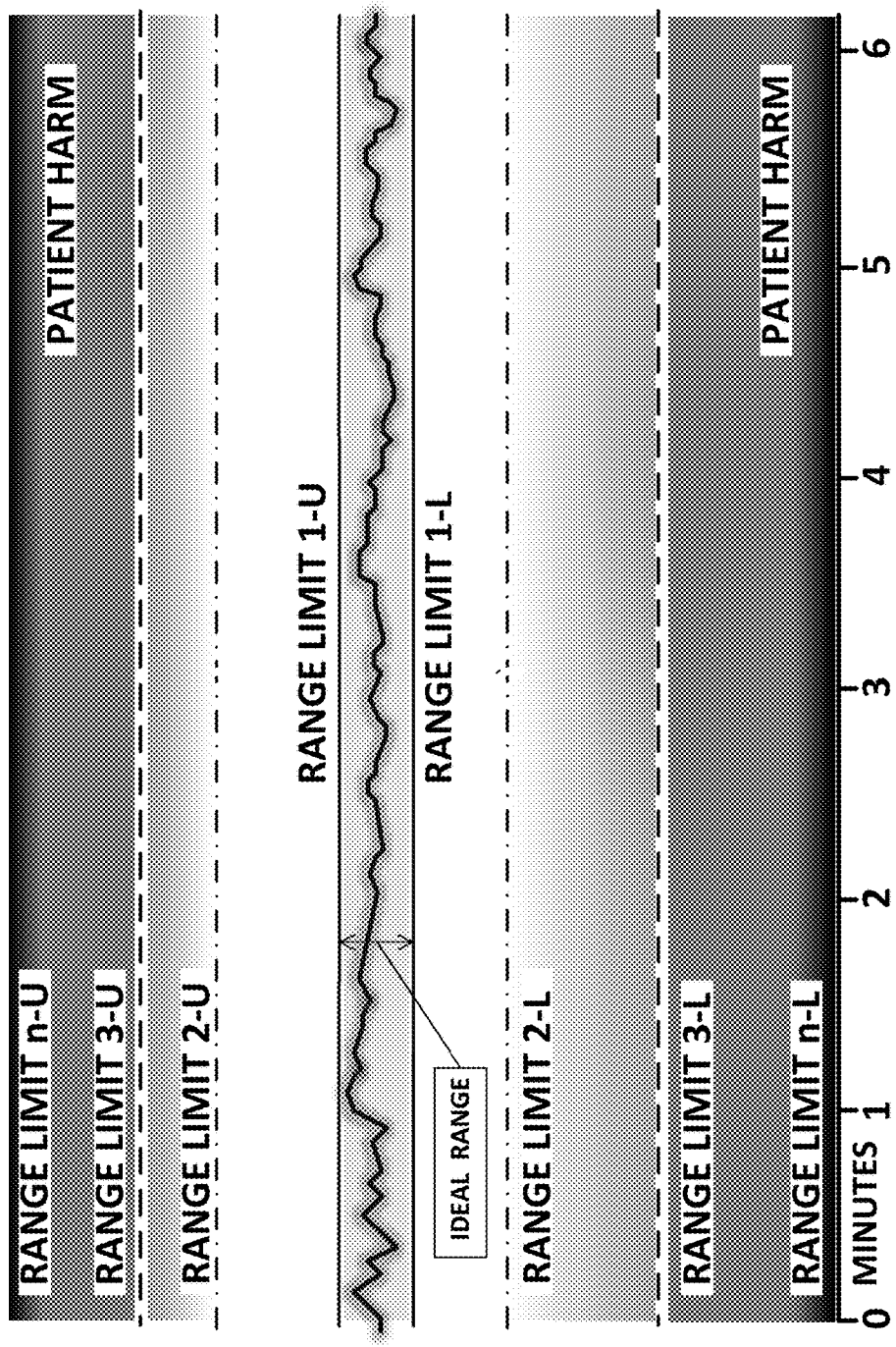
FIG. 7C is an exemplary graph of patient conditions during a semi-autonomous medical procedure.

FIG. 7C is an exemplary graph of patient conditions during a semi-autonomous medical procedure. As depicted, range limits exist on both sides of an ideal range (or "target range") for a particular parameter. The ideal range is a zone in which the disclosed technology generates information about, maintains the patient conditions within, optimizes based on each specific patient, and generates multiple upper and lower bounds. The range limits are not necessarily the same distance away (e.g., 2-L is closer to 1-L than 2-U is to 1-U). During a medical procedure, each of the patient conditions should remain within the upper and lower range markers Range Limit 1-U and Range Limit 1-L.

The disclosed technology and methods described herein are advantageous to predict future conditions of the patient as well as conditions of one or more parameters that are monitored during the procedure to determine procedure adjustments. The procedure adjustments can be generated in order to prevent the patient or any of the monitored parameters from leaving an associated ideal range (also referred to as a target range or a safety range). Thus, the patient or parameter conditions should not be in any region of patient harm or any range above the ideal range during the procedure.

During the procedure, the range limits can change. For example, the range limits can be pre-designed to change based on conditions predicted pre-procedure using the disclosed technology. In other examples, the range limits can change in real-time during the procedure, based on real-time changes in patient conditions, changes in monitored parameters, predictions made using the disclosed technology, and/or actions taken by the practitioner.

Figure 7D:
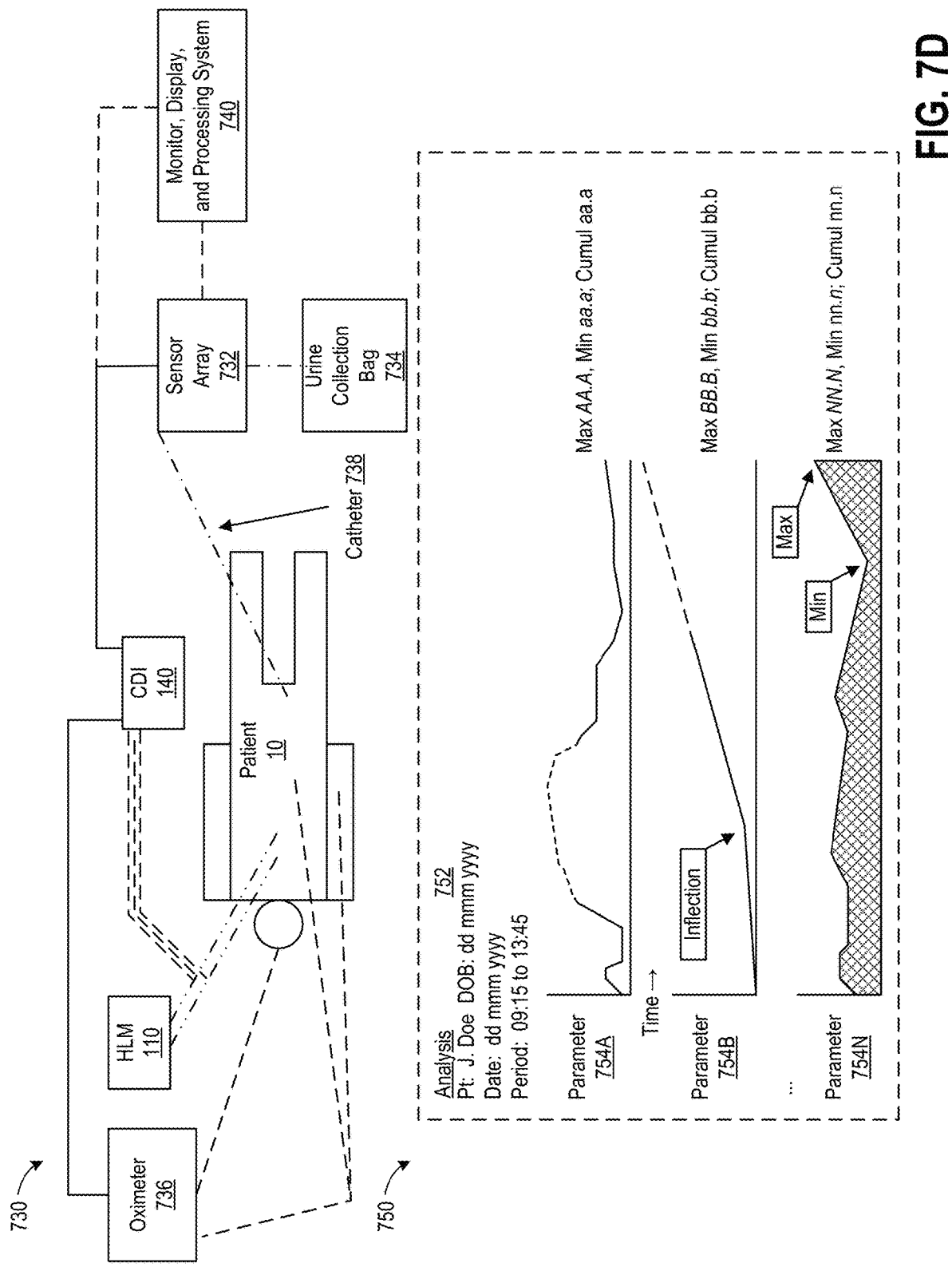
FIG. 7D is an exemplary schematic diagram of a patient undergoing a surgery with the example semi-autonomous computing system described herein.

FIG. 7D is an exemplary schematic diagram of the patient 10 undergoing procedure 730 with the example semi-autonomous computing system described herein. The patient 10 can be attached to one or more monitoring devices and procedure devices, including the HLM 110, the blood gas monitor 140, an oximeter 736, a sensor array 732, a catheter 738, and a urine collection bag 734. In this exemplary embodiment, a monitor, display, and processing system 740 can be used by a practitioner. The system 740 can include the HLM monitoring device 204 and the computing system 202, as depicted and described throughout this disclosure. As a result, some of the predicting of patient conditions and parameter levels can be performed at the same location as the practitioner who oversees the procedure 730. As described throughout this disclosure, predicting of one or more patient conditions and parameter levels can also be performed at computing systems in different locations that are in communication with the system 740. In other embodiments, the practitioner can use a monitoring device/display that is separate from the computing system (e.g., refer to FIGS. 2-3).

Each of the oximeter 736, HLM 110, blood gas monitor 140, sensor array 732, urine collection bag 734, and patient 10 can be continuously monitored by the system 740 before, during, and after the procedure 730. The system 740 can determine safety ranges (e.g., target ranges, ideal ranges) for parameters associated with each of these devices and the patient 10. As described throughout, the system 740 can predict whether any of the parameters associated with these devices and the patient 10 are expected to exceed the associated safety ranges, and if so, what procedure adjustment recommendations to make and provide to the practitioner.

Moreover, correlating historic data and real-time data about multiple devices that are used during the procedure 730 can allow for more accurate predictions of patient outcomes, patient safety, patient harm, and procedure adjustment recommendations. For example, the HLM 110's conditions can be monitored and automatically adjusted by the disclosed technology simultaneously with monitoring of the urine collection bag 734. The sensor array 732 can be a pass-through device as depicted (e.g., outflow from a patient passes through on its way to the collection bag 734), can be integrated with the collection bag 734, can be separate from the bag 734, as depicted, but in communication to/from the bag 734 and sensors, leads, etc., and/or any combination thereof. If the sensor 732 and/or sensor monitor is made aware of the collection bag 734's capacity, predictions of impending overfill can be generated by the system 740. Procedure adjustments and/or notifications can be provided to the practitioner before the bag 734 actually overflows, such that overflow can be avoided.

The system 740 can provide procedure information 750 to the practitioner at the monitor/display. The procedure information 750 can be updated in real-time as one or more conditions or parameters change based on actions taken by the practitioner in performing the procedure 730. The system 740 can also dynamically update and/or adjust safety ranges for each of the parameters and/or patient 10. Based on such changes in real-time, the system 740 can provide procedure adjustment recommendations to the practitioner in order to maintain each of the parameters and/or patient 10 within their associated safety ranges before, during, and after the procedure 730.

The procedure information 750 can include patient information 752 and information for each parameter and/or patient 10 being monitored during the procedure 730. For example, the patient information 752 can include a patient's name, birthday, date of procedure, and scheduled procedure time. Additional information can be included, such as pre-existing health conditions that may affect the procedure outcome. As depicted in FIG. 7D, parameters 754A-N can be included in the procedure information 750. One or more additional parameters that are being monitored can be depicted in the information 750. All the parameters 754A-N can be simultaneously maintained within their safety ranges. The quicker the response rate from the practitioner and/or the greater degree of AI autonomy, the greater the duration(s) during the procedure 730 where all parameters 754A-N are maintained within their safety ranges.

Each of the parameters 754A-N can be demonstrated using graphs. The graphs can indicate predictions or trends for the parameters 754A-N before, during, and after the procedure 730. One or more procedure adjustment recommendations can be made and displayed for each of the parameters 754A-N in the procedure information 750.

As described throughout, the safety ranges and range limits can be subject to general patients data and individual patient data, including pre-procedure response test data and/or procedure object data. Using the technology described herein, settings for range limits can be suggested, as displayed as the procedure information 750, to the practitioner. The practitioner can accept the settings and/or make the corresponding adjustments. The practitioner's adjustments can be recorded. These adjustments can be optionally and/or additionally displayed in the procedure information 750. For example, if an adjustment is made to the parameter 754A, the associated graph can be updated to reflect real-time changes. Updates can then be made to the algorithms or other techniques used to determine and suggest range limits (e.g., safety zones or ranges) based on the particular practitioner's adjustments, what other practitioners typically do, patient procedure data, patient outcome data, and other data sources as described herein.

As depicted in FIG. 7D, graphs for the parameters 754A-N show a level or a rate over time, complimented by display of other factors, such as minimum, maximum, present value, etc. Each parameter 754A-N's level or rate corresponds with units seen from an en masse analysis, with the cumulative value showing what an en masse analysis would eventually show retrospectively. The example of the parameter 754A depicts one of many advantages given by disclosed technology, which is continuous monitoring that indicates whether the parameter 754A is predicted to exceed an acceptable or safe level over time. As a result, the practitioner can be aware of potential climbs in value of the parameter 754A and address those climbs before those climbs occur.

As another example, parameter 754B's example graph depicts a cumulative situation, such as CPB surgery where hemoglobin has appeared in urine (e.g., hemoglobinuria). The graph can be predicted and generated based on continuous monitoring of the urine collection bag 734. Traditional en masse analysis would only reveal retrospectively that an unacceptable and possibly dangerous situation had occurred during the procedure 730. The disclosed technology not only alerts the practitioner that a threshold had been exceeded but also predicts the situation by reporting a rate change at the inflection point and providing procedure adjustment recommendations to the practitioner and/or automatically performing such procedure adjustment.

In a traditional medical procedure, an oxygenator reservoir (e.g., venous return reservoir) can reach a low level, thereby activating an alarm. A traditional system is routinely pre-programmed to immediately stop pumps, such as the arterial pump, when that alarm activates. When the arterial pump is automatically stopped, a patient endures zero perfusion (e.g., no oxygen delivery, no carbon dioxide removal) until the problem is manually resolved. Recovery is not instantaneous upon restarting flow from the oxygenator reservoir because, for example, the patient's metabolism has continued. This results in an oxygen deficit and carbon dioxide build up. Thus, oxygenator and flow rate settings must be reset and continuously adjusted by a practitioner until a time at which patient condition stability is returned.

The longer the patient is in the alarm state, the more challenging and longer it is to return the patient to a state of stability.

Using the disclosed technology, as described herein and in reference to FIG. 7D, the computing system 740 (e.g., computing system 202 in FIGS. 2-3) can automatically predict when the oxygen reservoir level is or will be dropping based on information received from the pump 111 flow rate and/or oxygenator reservoir level detectors before and/or during the procedure 730. Such predictions can be displayed in the procedure information 750 (e.g., parameter 754A can be associated with the oxygen reservoir). The computing system 740 can, for example, invoke and/or suggest to the practitioner a reduced pump speed, rather than wait for an alarm once the reservoir level hits zero.

As mentioned, the disclosed technology can be used to continuously monitor and predict conditions/parameters of any devices as well as generate procedure adjustments for any of those devices used during the medical procedure 730. For example, using the disclosed technology, data inputs and AI interpretation of these inputs can result in generating alerts, alarm conditions, procedure adjustments relative to blood level in a venous reservoir, air bubble activity in the vital blood paths of a CPB circuit, and system pressures in various parts of the circuit. The disclosed technology can also use the predicted conditions to automatically intervene in the procedure 730 to prevent patient harm by temporarily adjusting critical metabolic support pump functions. Earlier notifications can be transmitted to the practitioner to provide the practitioner with more time for procedure adjustment while an arterial pump or venous occluder, for example, initiates a response to changing conditions involving blood volume or system pressures. As a result, more consistent patient support can be provided for an efficient, lower stress practitioner response to the changing condition, which, if it were not for the autonomous procedure adjustment, could result in an interruption of metabolic support.

As yet another example, a rate of blood volume change in the HLM 110 can be continuously monitored and used by the disclosed technology to generate practitioner notifications. The disclosed technology can more accurately predict a time to empty and an optimal rate of arterial blood pump flow reduction. The predictions can be automatically implemented, which can result in maintaining a measure of support to the patient 10 while a problem with blood flow can be rectified and full cardiopulmonary bypass support can be resumed.

Figure 8A:
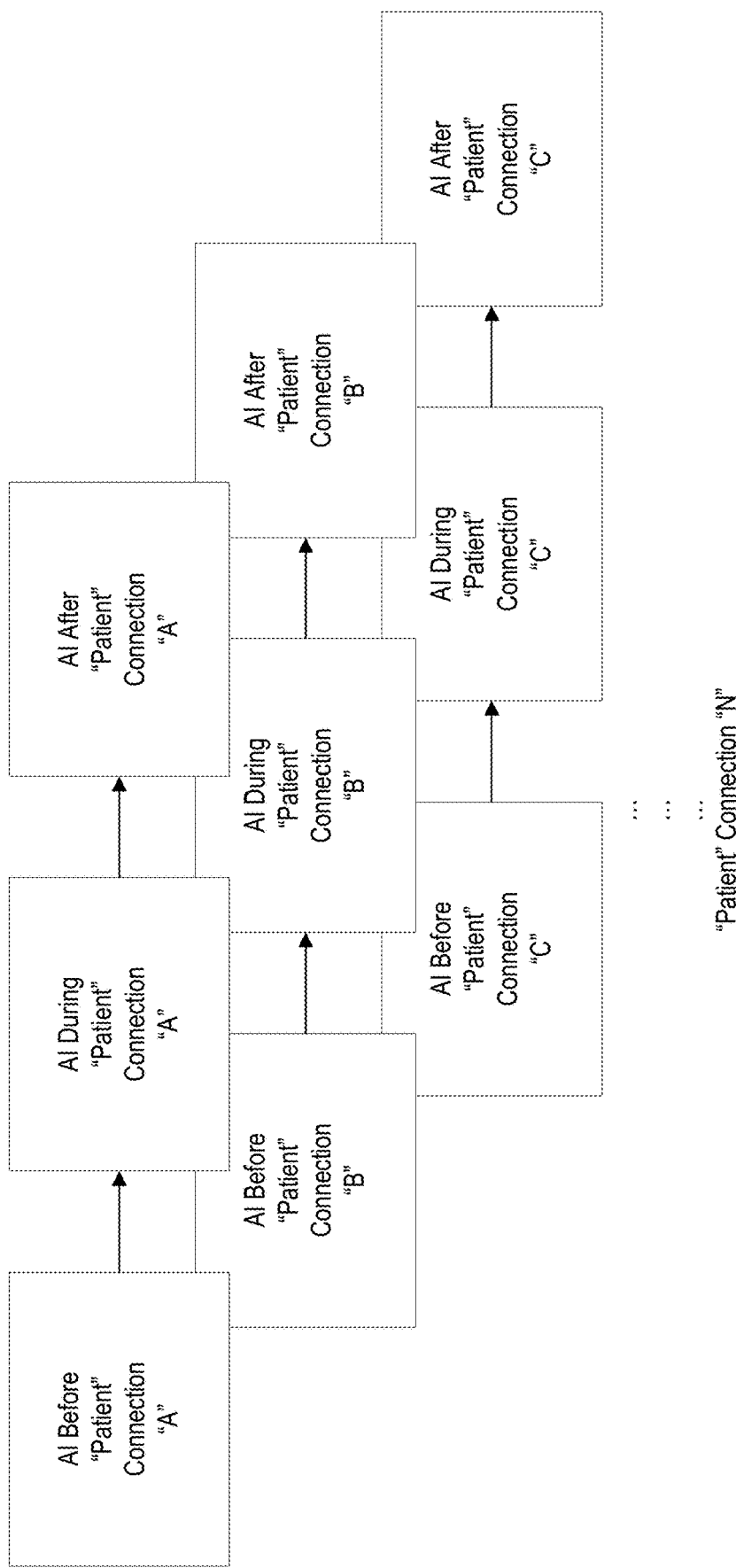
FIGS. 8A-8B are example block diagrams of different layers of patient condition predictions interacting with one another.
Figure 8B:
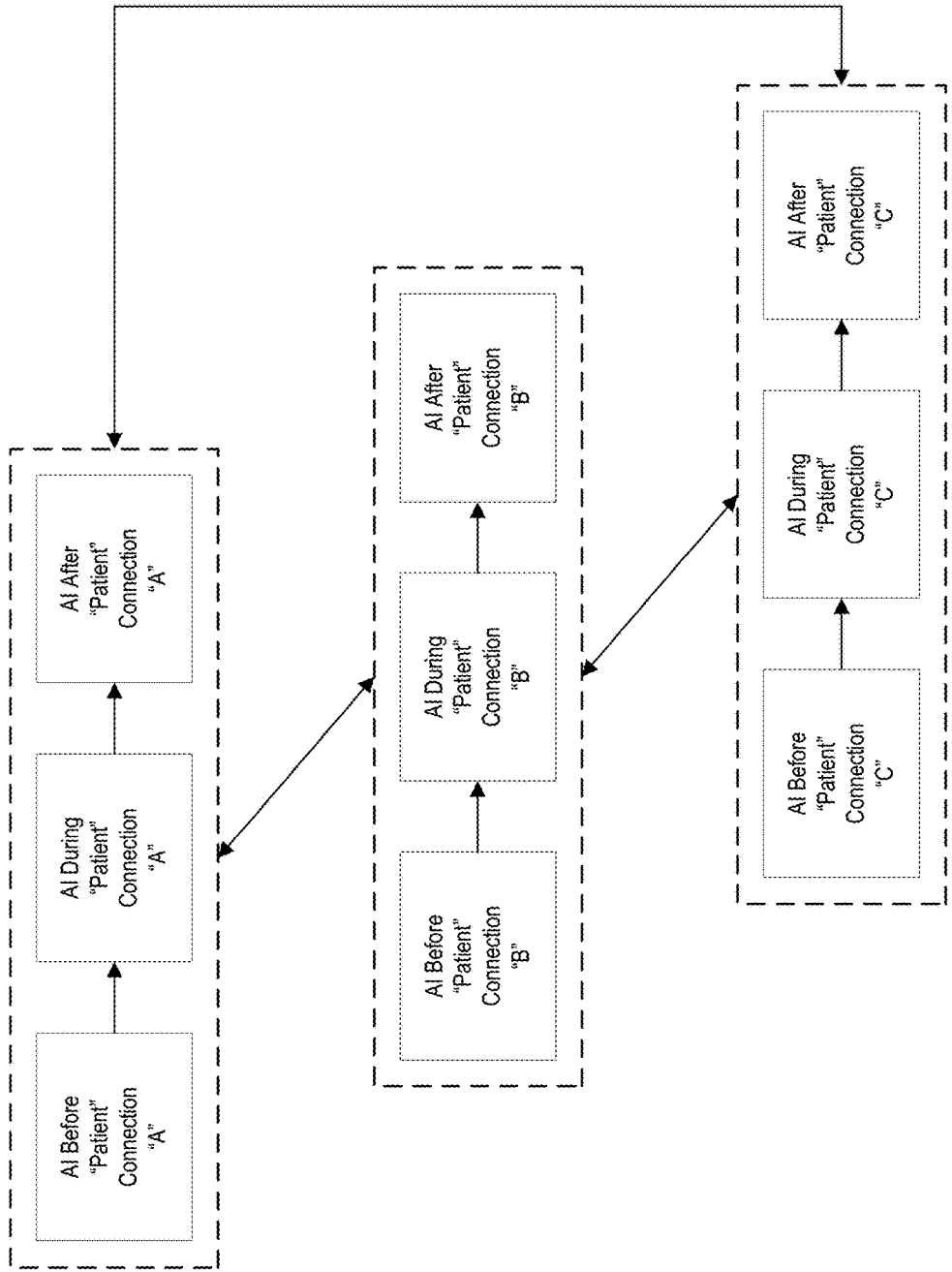

FIGS. 8A-8B are example block diagrams of different layers of patient condition predictions interacting with one another. FIG. 8A refers to different patient condition predictions as being layered. As depicted, the algorithms, AI, and other techniques described herein can be applied to different patients A-N, whether or not the patients A-N are located at a same facility, undergoing a same medical procedure, or being overseen by the same practitioner. Data and conditions that are sensed/collected/predicted during any one of the procedures for patients A-N can be used by the computing system in assessing and determining conditions/procedure adjustments for any of the other patients A-N. The computing system described herein can be remote from any one or all of the patients A-N procedures while maintaining high capacity and speed to more efficiently generate conditions and procedure adjustments for each of the patients A-N (e.g., refer to FIGS. 2A-2B).

FIG. 8B refers to interaction of one or more layers of patient condition predictions. Information associated with each of the patients can be transferred from remote locations of the patients and used by the computing system to predict each of the patients conditions and/or procedure adjustments (e.g., refer to FIGS. 2A-2B).

In some examples, each of the patients' locations can include a computing system that runs one or more predictive models on patient data. The patient location computing systems can each have their own specialty models. For example, Patient A's location computing system can have an advanced model of kidney function and metabolism. Patient B's location computing system can have an advanced model for liver monitoring. Patient C's location computing system can have an advanced model for spleen function. Those specialty models can then be accessed by patient computing systems at different patient locations as well as the computing system described herein (e.g., computing system 202 in FIG. 2).

Any of the patient location computing systems can be configured to support more than one procedure at more than one location. For example, Patient A's kidney can be monitored using the Patient A location computing system model. However, patient A's liver can be monitored using the Patient B location computing system model and patient A's spleen can be monitored using the Patient C location computing system model. As a result of such continuous connectivity and communication between different patient location computing systems and the computing system described herein, patient A's kidney, liver, and spleen conditions can be maintained within respective safety ranges/zones during patient A's medical procedure.

Embodiments of the subject matter and the operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer programs, i.e., one or more modules of computer program instructions, encoded on computer storage medium for execution by, or to control the operation of, data processing apparatus.

A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media (e.g., multiple CDs, disks, or other storage devices).

The operations described in this specification can be implemented as operations performed by a data processing apparatus on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., a FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's user device in response to requests received from the web browser.

Embodiments of the subject matter described in this specification can be implemented in a computing system that includes a back end component, e.g., as a data server, or that includes a middleware component, e.g., an application server, or that includes a front end component, e.g., a user computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), an internetwork (e.g., the Internet), and peer-to-peer networks (e.g., ad hoc peer-to-peer networks).

The computing system can include users and servers. A user and server are generally remote from each other and typically interact through a communication network. The relationship of user and server arises by virtue of computer programs running on the respective computers and having a user-server relationship to each other. In some embodiments, a server transmits data (e.g., an HTML page) to a user device (e.g., for purposes of displaying data to and receiving user input from a user interacting with the user device). Data generated at the user device (e.g., a result of the user interaction) can be received from the user device at the server.

While this specification contains many specific implementation details, these should not be construed as limitations on the scope of any inventions or of what may be claimed, but rather as descriptions of features specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A system for performing an open-heart surgical procedure on a patient, the system comprising:
a heart/lung machine;
one or more monitoring devices configured to monitor parameters indicative of conditions of the patient during the procedure;
a database storing:
first medical data describing medical information about the patient;
second medical data that summarizes health information of a general population of other patients; and
third medical data defining target ranges for operational parameters of the heart/lung machine and the one or more monitoring devices during the procedure; and
a computer system configured to receive in real-time during the procedure:
operational data from the heart/lung machine;
the parameters from the one or more monitoring devices;
the first medical data;
the second medical data; and
the third medical data,
the computer system further configured to, during the procedure, iteratively:
analyze: (i) the operational data from the heart/lung machine, (ii) the parameters from the one or more monitoring devices, (iii) the first medical data, and (iv) the second medical data; and
determine predictions, based on a comparison of the analysis of (i)-(iv) to the third medical data, that the operational data from the heart/lung machine or the parameters from the one or more monitoring devices are trending out of the target ranges,
wherein the computer system is further configured to generate, based on the predictions, a trained model for the procedure, wherein generating the trained model for the procedure comprises iteratively training a model for the procedure by correlating each of the predictions to (i) the operational data from the heart/lung machine, (ii) the parameters from the one or more monitoring devices, (iii) the first medical data, and (iv) the second medical data across one or more model layers using one or more machine learning algorithms, and wherein the computer system is further configured to determine the predictions that the operational data from the heart/lung machine or the parameters from the one or more monitoring devices are trending out of the target ranges based on applying the trained model for the procedure.

2. The system of claim 1, wherein the trained model is stored in the database.

3. The system of claim 1, wherein the computer system is further configured to generate, based on the predictions, recommended adjustments to be made in real-time during the procedure to at least one of the heart/lung machine or the one or more monitoring devices.

4. The system of claim 3, wherein the computer system is further configured to, in real-time during the procedure:
select one or more of the recommended adjustments based at least in part on analyzing (i) the operational data from the heart/lung machine, (ii) the parameters from the one or more monitoring devices, (iii) the first medical data, and (iv) the second medical data; and
autonomously implement the selected one or more recommended adjustments.

5. The system of claim 1, wherein the computer system is further configured to receive operational data from a plurality of heart/lung machines.

6. The system of claim 1, wherein the one or more monitoring devices include at least one of a camera or a sensor array.

7. The system of claim 1, wherein the one or more monitoring devices include a urine collection bag monitor.

8. The system of claim 1, wherein the first medical data includes current conditions of the patient and historic conditions of the patient.

9. The system of claim 1, wherein the second medical data includes historical health information of patients who have undergone the procedure.

10. A computer-implemented method for use while performing an open-heart surgical procedure on a patient, the method comprising:
receiving, by a computer system and in real-time during the procedure: (i) operational data from a heart/lung machine, (ii) parameters indicative of conditions of the patient during the procedure from one or more monitoring devices, (iii) first medical data describing medical information about the patient, (iv) second medical data that summarizes health information of a general population of other patients, and (v) third medical data defining target ranges for operational parameters of the heart/lung machine and the one or more monitoring devices during the procedure;
iteratively analyzing, by the computer system and during the procedure, (i)-(iv);
determining predictions, based on a comparison of the analysis of (i)-(iv) to the third medical data, that the operational data from the heart/lung machine or the parameters from the one or more monitoring devices are trending out of the target ranges; and
generating, based on the predictions, a trained model for the procedure, wherein generating the trained model for the procedure comprises iteratively training a model for the procedure by correlating each of the predictions to (i) the operational data from the heart/lung machine, (ii) the parameters from the one or more monitoring devices, (iii) the first medical data, and (iv) the second medical data across one or more model layers using one or more machine learning algorithms,
wherein the predictions are further determined based on applying the trained model for the procedure.

11. The method of claim 10, further comprising generating, based on the predictions, recommended adjustments to be made in real-time during the procedure to at least one of the heart/lung machine or the one or more monitoring devices.

12. The method of claim 11, further comprising selecting, by the computer system and during the procedure, one or more of the recommended adjustments based at least in part on analyzing (i) the operational data from the heart/lung machine, (ii) the parameters from the one or more monitoring devices, (iii) the first medical data, and (iv) the second medical data.

13. The method of claim 12, further comprising autonomously implementing, by the computer system and during the procedure, the selected one or more recommended adjustments.

\* \* \* \* \*